US007011768B2

(12) United States Patent
Jensen et al.

(10) Patent No.: US 7,011,768 B2
(45) Date of Patent: Mar. 14, 2006

(54) METHODS FOR HYDROGEN STORAGE USING DOPED ALANATE COMPOSITIONS

(75) Inventors: Craig M. Jensen, Honolulu, HI (US); Scott D. Redmond, San Francisco, CA (US)

(73) Assignee: FuelSell Technologies, Inc., San Francisco, CA (US)

( * ) Notice: Subject to any disclaimer, the term of this patent is extended or adjusted under 35 U.S.C. 154(b) by 133 days.

(21) Appl. No.: 10/463,352

(22) Filed: Jun. 16, 2003

(65) Prior Publication Data

US 2004/0009121 A1    Jan. 15, 2004

Related U.S. Application Data

(60) Provisional application No. 60/395,013, filed on Jul. 10, 2002.

(51) Int. Cl.
| | |
|---|---|
| *C01B 6/06* | (2006.01) |
| *C01B 6/24* | (2006.01) |
| *B01J 7/00* | (2006.01) |
| *C22C 21/00* | (2006.01) |
| *H01M 8/18* | (2006.01) |

(52) U.S. Cl. .......................... 252/188.25; 252/188.26; 252/188.27; 252/184; 48/61; 420/543; 420/900; 429/19; 429/20

(58) Field of Classification Search ................ 252/184, 252/188.25, 188.26, 188.27, 188.28, 950, 252/182.35; 48/61, 120, 190; 423/648.1, 423/644, 658.2; 429/19, 20, 22, 34; 420/900, 420/543
See application file for complete search history.

(56) References Cited

U.S. PATENT DOCUMENTS 1,226,205 A    5/1917  Graham 1,266,205 A    5/1918  Brock (Continued)

FOREIGN PATENT DOCUMENTS

WO    WO 97/19202    5/1997

(Continued)

OTHER PUBLICATIONS

The Hydrogen World View, Chapter 5, Advanced Engine Conversion Direct Cylinder Injection. Publisher: International Academy of Science, Publication Date:Dec. 1, 1991, ISBN: 096316340X, pp. 1-5.

(Continued)

*Primary Examiner*—Joseph D. Anthony
(74) *Attorney, Agent, or Firm*—Blakely Sokoloff Taylor & Zafman LLP

(57) ABSTRACT

The present invention concerns compositions, apparatus and methods for hydrogen storage. In certain embodiments, the compositions comprise sodium alanate and $\{\eta^5\text{-}C_5H_5\}_2TiH_2$. In preferred embodiments, the components of the composition are present in specified molar ratios, for example 0.7 NaH to 1.0 Al to 0.1 Ti. In various embodiments, the hydrocarbon rings coordinating the titanium are removed from the composition, for example by melting at 182° C. or higher or by cyclic discharge and recharge of hydrogen at temperatures of 100° C. or less. Methods for producing and using the claimed compositions are also provided. In various embodiments, the alanate composition may be stored, shipped and used in a modular container, such as a cassette. Exemplary hydrogen utilizing systems and methods for ordering, distribution and shipping of cassettes are also disclosed herein.

28 Claims, 8 Drawing Sheets

U.S. PATENT DOCUMENTS

| | | |
|---|---|---|
| 1,525,073 A | 2/1925 | Fotenot |
| 1,536,065 A | 5/1925 | Billings |
| 1,555,718 A | 9/1925 | Schroeder |
| 1,771,400 A | 7/1930 | Daubenspeck |
| 2,070,708 A | 2/1937 | Brokaw |
| 2,773,561 A | 12/1956 | Hunter |
| 3,165,099 A | 1/1965 | Vanderpool |
| 3,260,620 A | 7/1966 | Gruber |
| 3,357,864 A | 12/1967 | Huber |
| 3,432,354 A | 3/1969 | Jost |
| 3,436,270 A | 4/1969 | Oswin et al. |
| 3,454,429 A | 7/1969 | Gruber |
| 3,532,548 A | 10/1970 | Stachurski |
| 3,536,535 A | 10/1970 | Lippincott |
| 3,577,281 A | 5/1971 | Pountney et al. |
| 3,663,298 A | 5/1972 | McCoy et al. |
| 3,674,702 A | 7/1972 | Mackenzie et al. |
| 3,717,505 A | 2/1973 | Unkle, Jr. et al. |
| 3,822,149 A | 7/1974 | Hale |
| 3,842,248 A | 10/1974 | Yarnell et al. |
| 3,926,169 A | 12/1975 | Leshner et al. |
| 3,928,072 A | 12/1975 | Gerbier et al. |
| 3,932,600 A | 1/1976 | Gutbier et al. |
| 3,963,519 A | 6/1976 | Louie |
| 3,975,913 A | 8/1976 | Erickson |
| 3,977,990 A * | 8/1976 | Beckert et al. ............... 516/11 |
| 3,980,061 A | 9/1976 | McAlister |
| 4,000,003 A | 12/1976 | Baker et al. |
| 4,002,726 A | 1/1977 | Filby |
| 4,051,072 A | 9/1977 | Bedford et al. |
| 4,056,373 A | 11/1977 | Rubin |
| 4,085,590 A | 4/1978 | Powell et al. |
| 4,164,912 A | 8/1979 | Beylor |
| 4,185,979 A | 1/1980 | Woolley |
| 4,186,712 A | 2/1980 | Fitzner et al. |
| 4,211,537 A | 7/1980 | Teitel |
| 4,214,699 A | 7/1980 | Buchner et al. |
| 4,249,654 A | 2/1981 | Helverson |
| 4,302,179 A | 11/1981 | Pont |
| 4,319,552 A | 3/1982 | Sauer et al. |
| 4,343,272 A | 8/1982 | Buck |
| 4,359,396 A | 11/1982 | Maeland |
| 4,383,198 A | 5/1983 | Hosking |
| 4,406,867 A | 9/1983 | Marcinkowsky et al. |
| 4,415,512 A | 11/1983 | Torobin |
| 4,415,896 A | 11/1983 | Allgood |
| 4,431,520 A | 2/1984 | Giuliani et al. |
| 4,433,063 A | 2/1984 | Bernstein et al. |
| 4,436,537 A | 3/1984 | Turillon |
| 4,448,160 A | 5/1984 | Vosper |
| 4,459,270 A | 7/1984 | Leppard et al. |
| 4,468,854 A | 9/1984 | Chou et al. |
| 4,477,415 A | 10/1984 | Fecan et al. |
| 4,482,134 A | 11/1984 | Uda et al. |
| 4,489,049 A | 12/1984 | Forester et al. |
| 4,497,973 A | 2/1985 | Heath et al. |
| 4,537,761 A | 8/1985 | Reed et al. |
| 4,537,839 A | 8/1985 | Cameron |
| 4,546,740 A | 10/1985 | Clements et al. |
| 4,570,446 A | 2/1986 | Matsubara et al. |
| 4,589,919 A | 5/1986 | Goodell et al. |
| 4,599,867 A | 7/1986 | Retallick |
| 4,608,560 A | 8/1986 | Allgood |
| 4,608,830 A | 9/1986 | Peschka et al. |
| 4,613,362 A | 9/1986 | Welter et al. |
| 4,684,751 A | 8/1987 | Trogler et al. |
| 4,687,650 A | 8/1987 | Goodell et al. |
| 4,716,736 A | 1/1988 | Schwarz |
| 4,728,580 A | 3/1988 | Grasselli et al. |
| 4,757,456 A | 7/1988 | Benghiat et al. |
| 4,783,374 A | 11/1988 | Custer et al. |
| 4,793,980 A | 12/1988 | Torobin |
| 4,799,156 A | 1/1989 | Shavit et al. |
| 4,809,771 A | 3/1989 | Kennel et al. |
| 4,820,957 A | 4/1989 | Zivkoich |
| 4,867,785 A | 9/1989 | Keem et al. |
| 4,887,556 A | 12/1989 | Gladstone |
| 4,936,869 A | 6/1990 | Minderman et al. |
| 5,080,875 A | 1/1992 | Bernauer |
| 5,125,574 A | 6/1992 | Anderson et al. |
| 5,126,104 A | 6/1992 | Anand et al. |
| 5,217,506 A | 6/1993 | Edlund et al. |
| 5,219,678 A | 6/1993 | Hasebe et al. |
| 5,227,047 A | 7/1993 | Hwang |
| 5,248,649 A | 9/1993 | Mosley, Jr. |
| 5,250,368 A | 10/1993 | Golben et al. |
| 5,277,705 A | 1/1994 | Anderson et al. |
| 5,277,999 A | 1/1994 | Ovshinsky et al. |
| 5,283,572 A | 2/1994 | McClelland et al. |
| 5,296,438 A | 3/1994 | Heung |
| 5,315,531 A | 5/1994 | Oravetz et al. |
| 5,330,858 A | 7/1994 | Shundou et al. |
| 5,330,861 A | 7/1994 | Fetcenko et al. |
| 5,360,461 A | 11/1994 | Meinzer |
| 5,372,617 A | 12/1994 | Kerrebrock et al. |
| 5,372,629 A | 12/1994 | Anderson et al. |
| 5,383,113 A | 1/1995 | Kight et al. |
| 5,411,928 A | 5/1995 | Heung et al. |
| 5,443,616 A | 8/1995 | Congdon |
| 5,451,474 A | 9/1995 | Wu et al. |
| 5,456,740 A | 10/1995 | Snow et al. |
| 5,465,206 A | 11/1995 | Hilt et al. |
| 5,483,455 A | 1/1996 | Lay et al. |
| 5,495,239 A | 2/1996 | Ouellette |
| 5,499,279 A | 3/1996 | Chakraborty |
| 5,504,223 A | 4/1996 | Rosen et al. |
| 5,506,069 A | 4/1996 | Ovshinsky et al. |
| 5,512,787 A | 4/1996 | Dederick |
| 5,532,074 A | 7/1996 | Golben |
| 5,536,591 A | 7/1996 | Fetcenko et al. |
| 5,554,456 A | 9/1996 | Ovshinsky et al. |
| 5,557,254 A | 9/1996 | Johnson et al. |
| 5,572,438 A | 11/1996 | Ehlers et al. |
| 5,578,108 A | 11/1996 | Yamaguchi et al. |
| 5,590,197 A | 12/1996 | Chen et al. |
| 5,605,585 A | 2/1997 | Yamamoto et al. |
| 5,612,149 A | 3/1997 | Hartvigsen et al. |
| 5,616,432 A | 4/1997 | Ovshinsky et al. |
| 5,649,117 A | 7/1997 | Landry |
| 5,654,115 A | 8/1997 | Hasebe et al. |
| 5,654,886 A | 8/1997 | Zereski, Jr. et al. |
| 5,684,965 A | 11/1997 | Pickering |
| 5,688,611 A | 11/1997 | Golben |
| 5,696,906 A | 12/1997 | Peters et al. |
| 5,697,221 A | 12/1997 | Sapru et al. |
| 5,699,276 A | 12/1997 | Roos |
| 5,699,528 A | 12/1997 | Hogan |
| 5,702,491 A | 12/1997 | Long et al. |
| 5,703,257 A | 12/1997 | Rosen et al. |
| 5,710,889 A | 1/1998 | Clark et al. |
| 5,728,464 A | 3/1998 | Checketts |
| 5,738,953 A | 4/1998 | Lichtenberg et al. |
| 5,762,119 A | 6/1998 | Platz et al. |
| 5,771,946 A | 6/1998 | Kooy et al. |
| 5,778,972 A | 7/1998 | Sapru et al. |
| 5,780,701 A | 7/1998 | Kaska et al. |
| 5,797,269 A | 8/1998 | Nishimura et al. |
| 5,817,157 A | 10/1998 | Checketts |
| 5,840,437 A | 11/1998 | Diethelm |
| 5,840,440 A | 11/1998 | Ovshinsky et al. |
| 5,852,993 A | 12/1998 | Anderson |
| 5,882,611 A | 3/1999 | Williams et al. |
| 5,908,487 A | 6/1999 | Nishimura et al. |
| 5,932,372 A | 8/1999 | Rendina |

| | | |
|---|---|---|
| 5,943,656 A | 8/1999 | Crooks et al. |
| 5,961,697 A | 10/1999 | McManus et al. |
| 5,962,155 A | 10/1999 | Kuranaka et al. |
| 5,964,965 A | 10/1999 | Schulz et al. |
| 5,965,267 A | 10/1999 | Nolan et al. |
| 5,980,726 A | 11/1999 | Moulthrop, Jr. et al. |
| 5,987,895 A | 11/1999 | Nishimura et al. |
| 6,052,671 A | 4/2000 | Crooks et al. |
| 6,074,447 A | 6/2000 | Jensen |
| 6,074,453 A | 6/2000 | Anderson et al. |
| 6,086,729 A | 7/2000 | Bredsen et al. |
| 6,088,659 A | 7/2000 | Kelley et al. |
| 6,088,688 A | 7/2000 | Crooks et al. |
| 6,101,801 A * | 8/2000 | Boni ............................ 57/18 |
| 6,106,801 A | 8/2000 | Bogdanovic et al. |
| 6,119,651 A | 9/2000 | Anderson |
| 6,120,936 A | 9/2000 | Young et al. |
| 6,122,603 A | 9/2000 | Budike, Jr. et al. |
| 6,136,156 A | 10/2000 | El-Shall et al. |
| 6,139,302 A | 10/2000 | Wood et al. |
| 6,143,052 A | 11/2000 | KiyoKawa et al. |
| 6,152,995 A | 11/2000 | Edlund |
| 6,165,643 A | 12/2000 | Doyle et al. |
| 6,193,929 B1 | 2/2001 | Ovshinsky et al. |
| 6,194,092 B1 | 2/2001 | Ohara et al. |
| 6,197,990 B1 | 3/2001 | Oda et al. |
| 6,218,034 B1 | 4/2001 | Faris et al. |
| 6,221,310 B1 | 4/2001 | Checketts et al. |
| 6,228,519 B1 | 5/2001 | Faris et al. |
| 6,231,642 B1 | 5/2001 | Shelby et al. |
| 6,239,508 B1 | 5/2001 | Faris et al. |
| 6,245,280 B1 | 6/2001 | Tan et al. |
| 6,247,565 B1 | 6/2001 | Saint-Antonin et al. |
| 6,267,229 B1 | 7/2001 | Heung |
| 6,270,719 B1 | 8/2001 | Fetcenko et al. |
| 6,274,093 B1 | 8/2001 | Long et al. |
| 6,283,812 B1 | 9/2001 | Jin et al. |
| 6,296,960 B1 | 10/2001 | Faris et al. |
| 6,297,592 B1 | 10/2001 | Goren et al. |
| 6,299,997 B1 | 10/2001 | Faris et al. |
| 6,305,442 B1 | 10/2001 | Ovshinsky et al. |
| 6,306,339 B1 | 10/2001 | Kiyokawa et al. |
| 6,306,534 B1 | 10/2001 | Faris et al. |
| 6,309,771 B1 | 10/2001 | Faris et al. |
| 6,312,844 B1 | 11/2001 | Faris |
| 6,327,541 B1 | 12/2001 | Pitchford et al. |
| 6,328,821 B1 | 12/2001 | Ovshinsky et al. |
| 6,335,111 B1 | 1/2002 | Faris et al. |
| 6,365,292 B1 | 4/2002 | Faris et al. |
| 6,368,406 B1 | 4/2002 | Deevi et al. |
| 6,372,377 B1 | 4/2002 | Ovshinsky et al. |
| 6,376,115 B1 | 4/2002 | Tsai et al. |
| 6,378,601 B1 | 4/2002 | Ovshinsky et al. |
| 6,382,264 B1 | 5/2002 | Tsai et al. |
| 6,383,673 B1 | 5/2002 | Faris et al. |
| 6,387,152 B1 | 5/2002 | Klassen et al. |
| 6,395,405 B1 | 5/2002 | Buxbaum |
| 6,403,244 B1 | 6/2002 | Faris et al. |
| 6,403,772 B1 | 6/2002 | Ewen et al. |
| 6,410,174 B1 | 6/2002 | Faris |
| 6,413,670 B1 | 7/2002 | Ovshinsky et al. |
| 6,418,275 B1 | 7/2002 | Yang |
| 6,425,251 B1 | 7/2002 | Stetson et al. |
| 6,432,283 B1 | 8/2002 | Fairlie et al. |
| 6,444,016 B1 | 9/2002 | Oshima et al. |
| 6,451,463 B1 | 9/2002 | Tsai et al. |
| 6,461,766 B1 | 10/2002 | Young et al. |
| 6,471,935 B1 * | 10/2002 | Jensen et al. ............... 423/646 |
| 6,680,043 B1 * | 1/2004 | Yebka et al. ............. 423/648.1 |
| 6,793,909 B1 * | 9/2004 | Gross et al. ................ 423/644 |
| 2001/0051130 A1 * | 12/2001 | Jensen et al. ............... 423/644 |
| 2002/0029820 A1 | 3/2002 | Ovshinsky et al. |
| 2002/0073618 A1 | 6/2002 | Ovshinsky et al. |
| 2003/0026757 A1 | 2/2003 | Pecharsky et al. |
| 2003/0053948 A1 * | 3/2003 | Bogdanovic et al. ..... 423/658.2 |
| 2003/0143154 A1 * | 7/2003 | Gross et al. ................ 423/644 |
| 2003/0234010 A1 * | 12/2003 | Redmond .................... 123/575 |
| 2004/0009121 A1 | 1/2004 | Jensen et al. |
| 2004/0016769 A1 * | 1/2004 | Redmond ....................... 222/3 |
| 2004/0023087 A1 * | 2/2004 | Redmond ..................... 429/19 |
| 2004/0094134 A1 * | 5/2004 | Redmond et al. ........... 123/527 |
| 2004/0247521 A1 * | 12/2004 | Bogdanovic et al. ....... 423/644 |

FOREIGN PATENT DOCUMENTS

| | | |
|---|---|---|
| WO | WO 97/19481 | 5/1997 |
| WO | WO 97/21370 | 6/1997 |
| WO | WO 97/26214 | 7/1997 |
| WO | WO 97/36819 | 10/1997 |
| WO | WO 98/26459 | 6/1998 |
| WO | WO 98/50968 | 11/1998 |
| WO | WO 99/54517 | 10/1999 |
| WO | WO 99/55926 | 11/1999 |
| WO | WO 00/07930 | 2/2000 |
| WO | WO 00/13244 | 3/2000 |
| WO | WO 00/20329 | 4/2000 |
| WO | WO 00/61828 | 10/2000 |
| WO | WO 00/62360 | 10/2000 |
| WO | WO 00/66941 | 11/2000 |
| WO | WO 00/69773 | 11/2000 |
| WO | WO 00/70695 | 11/2000 |
| WO | WO 01/91210 | 11/2000 |
| WO | WO 00/79201 | 12/2000 |
| WO | WO 01/04973 | 1/2001 |
| WO | WO 01/16021 | 3/2001 |
| WO | WO 01/20697 | 3/2001 |
| WO | WO 01/34861 | 5/2001 |
| WO | WO 01/38591 | 5/2001 |
| WO | WO 01/39289 | 5/2001 |
| WO | WO 01/44713 | 6/2001 |
| WO | WO 01/44737 | 6/2001 |
| WO | WO 01/48837 | 7/2001 |
| WO | WO 01/81850 | 11/2001 |
| WO | WO 01/88455 | 11/2001 |
| WO | WO 01/92592 | 12/2001 |
| WO | WO 02/02835 | 1/2002 |
| WO | WO 02/07420 | 1/2002 |
| WO | WO 02/31897 | 4/2002 |
| WO | WO 02/31900 | 4/2002 |
| WO | WO 02/12118 | 7/2002 |
| WO | WO 02/56396 | 7/2002 |
| WO | WO 02/057006 | 7/2002 |
| WO | WO 02/066369 | 8/2002 |
| WO | WO 02/069419 | 9/2002 |
| WO | PCT/US03/08298 | 3/2003 |
| WO | PCT/US03/19950 | 6/2003 |

OTHER PUBLICATIONS

The Hydrogen World View, Chapter 7, Hydrogen Stored As Metal Hydride The Safest Fuel on Earth.Publisher: International Academy of Science, Publication Date:Dec. 1, 1991, ISBN: 096316340X, pp. 1-11.

The Hydrogen World View, Chapter 11, The Hydrogen Fuel Cell Efficiency if the Key. Publisher: International Academy of Science, Publication Date:Dec. 1, 1991, ISBN: 096316340X, pp. 1-10.

F.E. Lynch. International Academamy of Science—Hydrogen Tech Papers. 74001—Backfire Control Techniques For Hydrogen Fueled Internal Combustion Engines. [online] [retrieved on Aug. 18, 2003] Retrieved at http://www.science.edu/tech/h74001.htm. pp. 1-9.

Texaco Ovonic Hydrogen Solutions. N.Stetson et al., "Material Classification Regulations and their Impact on Reversible Metal Hydride Hydrogen Storage Systems", [online]

Retrieved on Apr. 29, 2003 Retrieved from the Internet at: http://www.ovohi.com. pp. 1-18.

Texaco Ovonic Hydrogen Solutions.We help fuel imaginiations. [online] Retreived on Apr. 29, 2003. Retrieved from the Internet: http://www.ovonic.com/sol_srv/3_3_hydrogen_sol.htm. pp. 1-8.

Texaco Ovonic Hydrogen Solutions.Ovonic Solid-State Hydrogen Bulk Storage System. [online] Retrieved on Apr. 29, 2003. Retrieved from the Internet at: http://www.ovonic.com/PDFs/HydrogenSpecSheet/ovonic_hydrogen_spec_032103.pdf. p. 1.

Dr. Rosa C. Young, Texaco Ovonic Hydrogen Systems, LLC. Advances of Solid Hydrogen Storage Systems. 14th Annual Conference of NHA, Mar. 4-6, 2003.pp. 1-16.

FST, Inc. Unveils Hydrogen Energy Appliance, Line of Hydrogen Products to Power Cars, Electrical Generators, Remote & Back-Up Power. Press Release, San Francisco, California, Oct. 15, 2002, 2 Pages.

PRWeb™. The Free Wire Service, Mar. 28, 2002. [online] [retrieved on Dec. 5, 2002] New Energy Company to Deliver Inexpensive Power For Your Car, Home or Business by Mail. Retrieved from the Internet:<URL:http:/www.prweb.com/releases/2002/3/prweb35853.php, 1 page.

Wade A. Amos; National Renewable Energy Laboratory, "Costs of Storing and Transporting Hydrogen". Nov. 1998, NREL/TP-570-25106, pp. 1-59.

J. Philip DiPietro, et al., Energetics, Incorporated, Oct. 29, 1999. "Analysis of the Sodium Hydride-based Hydrogen Storage System", Proceedings of the 2000 DOE Hydrogen Program Review, NREL/CP-570-28890 (2000), pp. 861-888.

Borislav Bogdanovic, et al. "Ti-doped alkali metal aluminium hydrides as potential novel reversible hydrogen storage materials", Journal of Alloys and Compounds 253-254 (1997) pp. 1-9.

K.J. Gross, et al. "Dynamic in situ X-ray diffraction of catalyzed alanates", Journal of Alloys and Compounds 330-322 (2002) pp. 691-695.

G. Sandrock, et al., "Engineering considerations in the use of catalyzed sodium alanates for hydrogen storage", Journal of Alloys and Compounds 330-322 (2002) pp. 696-701.

Borislav Bogdanovic, et al. "Ti-doped $NaAlH_4$ as a hydrogen-storage material—preparation by Ti-catalyzed hydrogenation of aluminum powder in conjunction with sodium hydride", Applied Physics A, 72:221, 2001, pp. 221-223.

Borislav Bogdanovic, et al., "Metal-doped sodium aluminum hydrides as potential new hydrogen storage materials", Journal of Alloys and Compounds 302 (2000) pp. 36-58.

Karl. J. Gross, et al., "In-situ X-ray diffraction study of the decomposition of $NaAlH_4$", Journal of Alloys and Compounds 297 (2000) pp. 270-281.

A. Zaluska, et al., "Structure, catalysis and atomic reactions on the nona-scale: a systematic approach to metal hydrides for hydrogen storage", Aaplied Physics A, 72:157-165, 2001.

Craig M. Jensen, et al., "Advanced titanium doping of sodium aluminum hydride: segue to a practical hydrogen storage material?", International Journal of Hydrogen Energy 24 (1999) pp. 461-465.

C. Sachs, et al., "Solubility of hydrogen in single-sized palladium clusters", Physical Review B. vol. 64, 075408 (2001) pp. 1-10.

Craig M. Jensen, et al., "Catalytically Enhanced Systems For Hydrogen Storage", Proceedings of the 2001 DOE Hydrogen Program Review NREL/CP-570-30535, pp. 1-9. Department of Chemistry, University of Hawaii.

Craig M. Jensen, et al., "Catalytically Enhanced Systems For Hydrogen Storage", Proceedings of the 2001 DOE Hydrogen Program Review NREL/CP-57028890, pp. 1-6. Department of Chemistry, University of Hawaii.

K.J. Gross, et al. "Light-Weight Hydride Development", Proceedings of the 2001 DOE Hydrogen Program Review NREL/CP-570-30535, pp. 1-14. Sandia National Laboratories, Livermore, California.

The Organometallic HyperTextBook: Cyclopentadienyl Ligands [online] [retrieved on Jun. 16, 2002] Retrieved from the Internet:<http://www.ilpi.com/organomet/cp.html.

Craig M. Jensen, et al., "Hydrogen Storage Via Caltytically Enhanced Metal Hydrides", Proceedings of the 1999 U.S. DOE Hydrogen Program Review NREL/CP-570-26938, pp. 1-6.

H2 Information Network: Hydrogen-Fuel Cells for Transportation—Fuels for Fuel Cells—2002 Annual Program/Lab R&D Review.May 6-8, 2002. [online] [retrieved on Jun. 2, 2002] Retrieved from the Internet: <http://www.eren.doe.gov/hydrogen/hydrogen_review.html. pp. 1-3.

H2 Information Network: HTAP Apr. 16-17, 2001 Meeting Minutes; Hydrogen Technical Advisory Panel. [online] [retrieved on Apr. 18, 2002] Retrieved on the Internet: <http://www.eren.doe.gov/hydrogen/docs/htap_minutes_spring01.html. pp. 1-12.

SNL/CA—Engineered Materials Department. [online] [retrieved on Apr. 18, 2002] Retrieved on the Internet:<http://www.ca.sandia.gov/Materials&Engineering Sciences/EngMat/dept_pg.html. pp. 1-2.

Matthias Driess, "From molecular aggregates to novel organosilicon and phosphorus/arsenic compounds". Pure Appl. Chem., vol. 71, No. 3, pp. 437-443, 1999.

Hytek Microsystems HY-7110 Micro-heater, "Minature Proportionally Controlled Heater". pp. 33-34.

Hytek Microsystems HY-7115 Micro-heater, 5V, "Minature Proportionally Controlled Heater". pp. 13-14.

EV World Nano, Nano!-Part 2. [online] [retrieved on Sep. 6, 2002] Retrieved on theInternet:<http://evworld.com/databases/storybuilder.cfm?storyid=400&subcookie=1. pp. 1-4.

Science & Technology Corporation @ UNM.UNM—604, Power of plasma production of metallic namoparticles. J. Phillips, et al. [online] [retrieved on Jul. 23, 2002] Retrieved from the Internet:<http://stc.unm.edu/portfolio/abstract.cfm?docket=UNM-604, 1 page.

FuelCellStore.com's Hydrogen Storage Products Page. [online] [retrieved on Aug. 23, 2002] Retrieved on the Internet:<http://www.fuelcellstore.com/products/index/hydrogen_storage.html. pp. 1-2.

FuelCellStore.com Hydride Storage Tanks. Solid-H tm, Metal Hydride Hydrogen Storage Tanks, Product Description. [online] [retrieved on Aug. 23, 2002] Retrieved from the Internet:<http://www.fuelcellstore.com/products/hci/product_desc.htm. pp. 1-3.

Millenium Cell—Our Technology Solutions—White Paper [online] [retreived on Sep. 25, 2002] The Hydrogen on Demand™ System. Retrieved from the Internet:<http://www.millenniumcell.com/solutions/white_hydrogen.html. pp. 1-2.

Thermofoil (TM) Flexible Heating Elements—Minco. [online] [retrieved on Jul. 18, 2002] Retrieved on the Internet:<http://www.minco.com/heaters.php. pp. 1-3.
MINCO—Thermofoil™ Heater/Sensors. Bulletin TF-9. pp. 1-2.
Minature Metal Foil Heaters and RTD Combinations at JP Technologies, Inc. [online] [retrieved on Jul. 23, 2002] Retrieved from the Internet:<http://www.jptechnologies.com/mmfhrtdcomb.html. pp. 1-4.
Z. Turgut, et al. "Magnetic properties and microstructural observations of oxide coated FeCo nanocrystals before and after compaction". Journal of Applied Physics, vol. 85, No. 8. Apr. 15, 1999. pp. 4406-4408.
F. Barbir, Hydrogen Conversion Technolgies, Review of hydrogen conversion technologies, Clean Energy Research Institute, University of Miami, Florida, pp. 1-17.
EyeforFuelCells-Facilitating the commercialisation of Fuel Cell technology. Press Release, Proton Energy Announces Major Breakthrough in Hydrogen Generation. Nov. 15, 2001. pp. 1-2.
Commuter Chronicles. Michael McCabe, Hydrogen-driven Revolution—not your father's SUV: Hypercar's sleek design is making waves. Monday Feb. 25, 2002. p. 1.
Jerry Flint, Backseat Driver. "Hydrogen Bomb"; Forbes Magazine, Mar. 4, 2002. p. 100.
Yes, You Can Buy This Home Fuel Cell. Popular Science, Feb. 2002.p. 10
Powerball Technologies—Sodium Production and Hydrogen Delivery. The Powerball Concept. . . [online] [retrieved on Dec. 13, 2002] Retrieved from the Internet: <http://www.powerball.net/concept/index.shtml.p. 1.
Powerball Technologies—Hydrogen Storage and Delivery System Specifications. Powerball System . . . [online] [retreived on Dec. 13, 2002] Retrieved from the Internet: <http://www.Powerball.net/order/index.html. p. 1.
Powerball Technologies—Distribution for a Workable Hydrogen Economy. The Powerball process is safe, clean and 100% recycleable. [online] [retrievd on Dec. 13, 2002] Retrieved from the Internet:<http://www.powerball.net/process/index.html. pp. 1-2.
Proceedings National Hydrogen Vision Meeting. Washington, D.C. Nov. 15-16, 2001. Energitics, Incorporated. pp. 1-24.
A. Zaluska, et al. "Sodium alanates for reversible hydrogen storage". Journal of Alloys and Compounds 298 (2000) pp. 125-134.
R. Zidan, et al. "Hydrogen cycling behavior of zirconium and titanium-zirconium-doped sodium aluminum hydride". Journal of Alloys and Compounds 285 (1999) pp. 119-122.
Arnold, Dr. Gerd, Advanced Hydrogen Storage Technologies, Global Alternative Propulsion Center (GAPC) GM, 10 pages.
Catelli, Brian, Chief of Staff to the Assistant Secretary of the Office of Energy Efficeincy and Renewable Energy to The Attendees of the Coal Hydrogen Workshop, Sep. 19, 2000, 10 pages.
Gross, K.J., et al. Hydride Development for Hydrogen Storage, Proceedings of the 2000 Hydrogen Program Review, NREL/CP-570-28890, 16 pages.
Niedzwiecki, Alan, Hydrogen Storage, Hydrogen Vision Meeting, QUANTUM Technologies Worldwide, Inc. Nov. 2001, 23 pages.
Chemistry 242-Inorganic Chemistry II, Chapter 9—Hydrogen, CHEM242-1999 Chapter 9 Course Notes. Retrieved on Apr. 17, 2002. Retrieved from the Internet: http://artsandscience.concordia.ca/facstaff/A-C/BIRD/c242/notes_ch9-cwp.html, 6 pages.
Metal hydrides as hydrogen storage system for fuel cells, Fabien Nion-Carles Guillen Amigo, EEIGM projet 2001, 40 pages.
AddALL.com—Roger E. Billings: Hydrogen World View. [online] [retrieved on Aug. 18, 2003] Retrieved from: www.addall.com/Browse.Detail/096316340X.html. 1 page.

* cited by examiner

METHODS FOR HYDROGEN STORAGE USING DOPED ALANATE COMPOSITIONS

BACKGROUND OF THE INVENTION

This application claims the benefit under 35 U.S.C. §119 (e) of provisional Patent Application Ser. No. 60/395,013, filed on Jul. 10, 2002.

FIELD OF THE INVENTION

The present invention relates to the field of hydrogen storage. More particularly, the present invention concerns methods and compositions for hydrogen storage using doped sodium aluminum hydride (sodium alanate).

DESCRIPTION OF RELATED ART

The widespread use of fossil fuel combustion and internal combustion engine (ICE) vehicles has created significant air quality problems in most of the industrialized world. Air pollution in turn is related to numerous health and environmental problems, including serious respiratory illnesses that can result in death. A variety of alternative energy sources, such as nuclear, solar, geothermal and wind power have been proposed to supplement and/or replace fossil fuel consumption. Drawbacks exist to each of these alternative energy sources.

One of the most promising non-polluting fossil fuel alternatives is hydrogen. Hydrogen can be combined with oxygen via combustion or through fuel cell mediated redox reactions to produce heat, electrical power and/or to power vehicles. The product of this reaction—water—is non-polluting and can be recycled to regenerate hydrogen and oxygen.

A serious limitation to the practical implementation of a hydrogen-powered economy is the ability to store and release sufficient amounts of hydrogen. Many alternative forms of hydrogen storage have been proposed, including pressurized hydrogen gas, liquid hydrogen, hydrogen storing metal halides, water activated borohydrides, carbon nanotubes, fullerenes and activated charcoal. Problems with the practical use of such forms of hydrogen storage include the need for large, bulky and heavy storage tanks, low capacity for hydrogen storage, low weight percent of hydrogen storage, high cost, difficulty of manufacture, low temperature storage requirements, safety issues, lack of long-term recycling capacity for hydrogen discharge and recharge, and the need for very high temperatures (up to several hundred degrees C.) to release hydrogen. An ideal hydrogen storage system would be inexpensive, could be repeatedly charged and discharged without breaking down, would exhibit fairly rapid hydrogen uptake and release, could store a high weight percent of hydrogen (preferably >4 wt. %), could operate at temperatures of about 100° C. or less and would not add a great deal of weight to hydrogen powered vehicles.

One of the most promising hydrogen storage systems in terms of the above characteristics is doped sodium alanate ($NaAlH_4$). Bogdanovic et al. (J. Alloys and Compounds, 253:1, 1997) demonstrated that alkali metal alanates could reversibly absorb and release hydrogen under relatively mild conditions when doped with transition metal catalysts, such as titanium. More recent studies have further characterized the kinetics, reaction pathway, recycling characteristics and the effects of various dopants on hydrogen uptake and release by doped sodium alanate compounds (e.g., Bogdanovic et al., J. Alloys and Compounds, 302:36, 2000; Bogdanovic et al., Applied Physics A, 72:221, 2001; Gross et al., J. Alloys and Compounds, 297:270, 1999a; Gross et al., in *Proceedings U.S. DOE Hydrogen Program Review*, NREL/CP-570-26938, 1999b; Gross et al., in *Proceedings U.S. DOE Hydrogen Program Review*, NREL/CP-570-28890, 2000; Gross et al., in *Proceedings U.S. DOE Hydrogen Program Review*, NREL/CP-570-30535, 2001; Jensen et al., Int. J. Hydrogen Energy, 24:461, 1999; Jensen et al., Applied Physics A, 72:221, 2001; Sandrock et al., in *Proceedings of the International Symposium on Metal Hydrogen Systems*, Noosa, Australia, October 2000; Thomas et al., in *Proceedings U.S. DOE Hydrogen Program Review*, NREL/CP-570-26938,452, Denver, Colo. 1999; Zaluska et al., J. Alloys and Compounds, 298:125, 2000; Zaluska et al., Applied Physics A, 72:157, 2001; Zidan et al., J. Alloys and Compounds, 285:119, 1999). Although progress has been made in this hydrogen storage system, further improvements are required to increase the maximum wt. % (weight percent) of hydrogen storage, decrease the cost and complexity of production and increase the amount of hydrogen released at 100° C. or less.

SUMMARY OF THE INVENTION

The invention generally concerns compositions, methods and apparatus for hydrogen storage. In certain embodiments, the invention concerns a novel doped sodium alanate composition. In preferred embodiments, the sodium alanate is doped with $\{\eta^5-C_5H_5\}_2TiH_2$. In various embodiments, the ratios of compounds in the composition are determined to provide maximum hydrogen weight percent storage. In one embodiment, the molar ratios of sodium to aluminum to titanium in the composition are 0.7:1.0:0.1. Those ratios are not limiting and other exemplary molar ratios are disclosed herein.

Some embodiments of the invention concern methods for making doped sodium alanate compositions. In a preferred embodiment, the composition is made by heating a mixture of the ingredients to 182° C. or higher, for 5 to 30 min. Heating results in the production of a sintered porous solid doped sodium alanate composition.

Other embodiments of the invention concern cassettes for holding, storing, shipping and using the doped sodium alanate composition. The cassettes may comprise various subunits, such as valves, heating elements, smart chips and RTDs (resistance temperature detectors). The composition of the cassette is impact resistant, corrosion resistant, waterproof, gas leak proof and lightweight. In certain embodiments, the cassette may withstand up to 10 atmospheres of internal pressure and may be constructed of materials to minimize heat loss from the inside of the cassette. In certain embodiments, the cassettes are modular and interchangeable.

In some embodiments, the compositions and apparatus may be used with a variety of hydrogen utilizing systems, including but not limited to vehicles, portable electrical generators, emergency electrical generators, disposable power supplies, fuel cells, catalytic heaters, hydrogen combustion systems and portable electronic devices.

In other embodiments, the invention concerns methods for tracking, ordering, shipping and distributing cassettes or other modules containing the claimed compositions.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

DESCRIPTION OF ILLUSTRATIVE EMBODIMENTS

Figure 1:
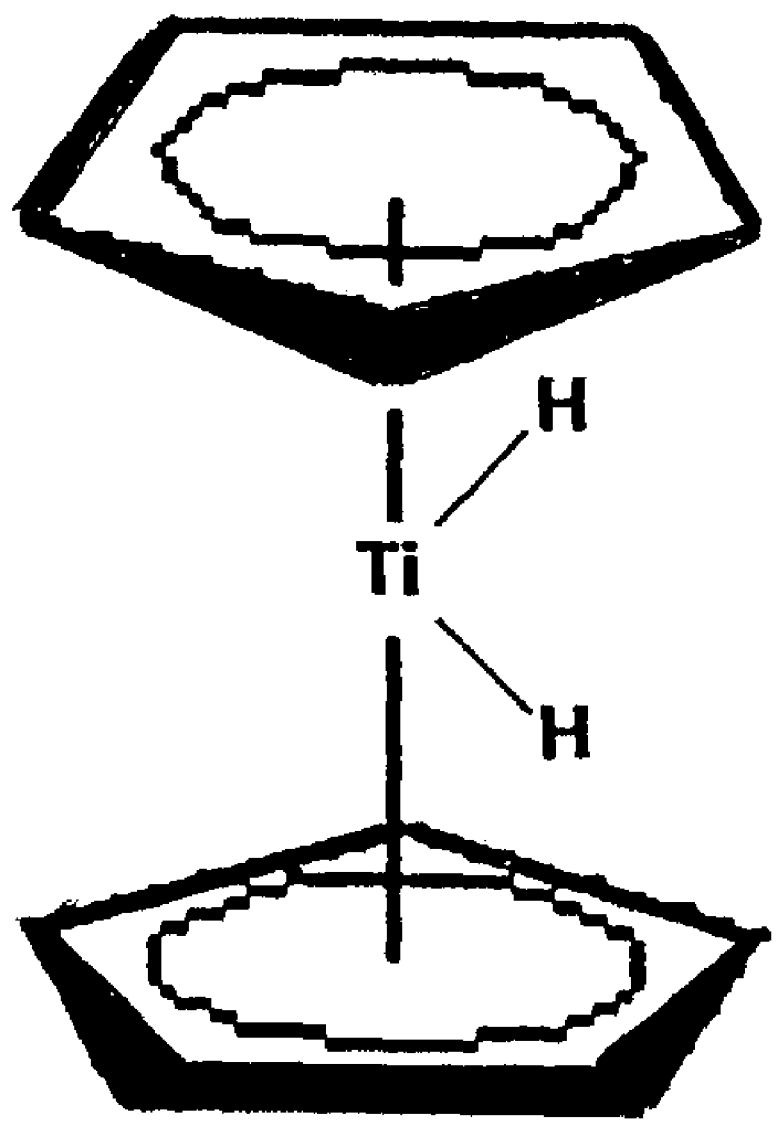
FIG. 1 shows the structure of an exemplary dopant.

As used herein, "a" or "an" may mean one or more than one of an item. Terms that are not otherwise defined herein are used in accordance with their plain and ordinary meaning. In the following detailed description, numerous specific details are set forth in order to provide a thorough understanding of the present invention. However, it will be apparent to one of ordinary skill in the art that these specific details need not be used to practice the present invention. In other circumstances, well-known structures, compounds, circuits, processes and interfaces have not been shown or described in detail in order not to unnecessarily obscure the present invention.

Uptake and Release of Hydrogen by Sodium Alanate

The reaction pathway for absorption and release of hydrogen for doped sodium alanate is as shown below.

$$3\ NaAlH_4 \rightarrow Na_3AlH_6 + 2Al + 3H_2 \quad \text{(Eq. 1)}$$

$$Na_3AlH_6 \rightarrow 3NaH + Al + 3/2H_2 \quad \text{(Eq. 2)}$$

The dehydrogenation of $NaAlH_4$ is thermodynamically favorable, with 1 atmosphere (atm) of desorption pressure reported at 33° C. using $NaAlH_4$ doped with 2 mol % each of the transition metal alkoxides $Ti(OBu^n)_4$ and $Zr(OPr)_4$ (Gross et al., 2000). However, the dehydrogenation of $Na_3AlH_6$ is less favorable, with 1 atm of desorption pressure estimated to occur at about 110° C. (Gross et al., 2000). As a practical matter, at a target operating temperature of 100° C. or less, hydrogen release from doped sodium alanate is limited primarily to the first reaction (Eq. 1), with a theoretical maximum release of 3.6 wt. % hydrogen. To release an additional 1.6 wt. % of hydrogen from the second reaction (Eq. 2) would require an operating temperature in excess of about 125° C.

Alternative alkali metal alanates have been investigated. For example, potassium alanate ($KAlH_4$) was reported to reversibly absorb and release hydrogen, but only 0.8 wt. % of hydrogen could be generated at up to 320° C. (U.S. Pat. No. 6,106,801).

Department of Energy (DOE) targets for advanced hydrogen storage technologies call for the release of 6.0 wt. % of hydrogen at an operating temperature of 100° C. or less. These targets are not achievable using present technologies for alkali metal alanate systems. In order to achieve the DOE targets, it will be necessary to make substantial improvements in the compositions and methods used with alanates. In preferred embodiments, the compositions and methods of the present invention comprise doped sodium alanate.

Dopants

A variety of dopants have been examined for use with alkali metal alanates. Bogdanovic (U.S. Pat. No. 6,106,801) disclosed the use of $TiCl_3$, $TiCl_4$, HTiCl, titanium tetra-n-butylate ($Ti(OBu)_4$, $Cp_2ZrCl_2$, $ZrCl_4$, $Cp_2Zr_2$, $VCl_3$, $Cp_2VCl_2$, $VCl_3$, $Cp_2VCl_2$, $NbCl_3$, $YCl_3$, $LaCl_3$, $CeCl_3$, $PrCl_3$, $NdCl_3$, $SmCl_3$, $FeCl_2$. $NiCl_2$ and $LaNi_5$ as dopants of sodium alanate, potassium alanate and $Na_2LiAlH_6$, using about 2 mol % of dopant. The doped compositions were prepared by mixing the components in organic solvent (ether) and vacuum removal of the solvent, or by magnetic stirring of the dry powder. Although doping significantly improved the hydrogen storage capacity of the alkali metal alanates, the doped materials exhibited fairly slow rates of hydrogen uptake and release. Release of hydrogen from $Na_3AlH_6$ required 4 to 5 hours at 160° C. and recharge of NaH and Al to $NaAlH_4$ took up to 15 hours at 170° C. Such slow rates of hydrogen discharge and recharge would provide serious limitations, for example, for a hydrogen powered vehicle.

Improvements in the doping procedure have been reported. Jensen et al. (in *Proceedings U.S. DOE Hydrogen Program Review*, NREL/CP-570-26938, 1999) observed that zirconium is inferior to titanium as a catalyst for dehydriding $NaAlH_4$ (Eq. 1), but was superior to titanium as a catalyst for dehydriding $Na_3AlH_6$ (Eq. 2). Sodium alanate that was doped with 1 mol % each of $Zr(Opr)_4$ and $Ti(OBu^n)_4$ exhibited improved hydrogen storage characteristics, with up to 4.5 wt. % of hydrogen released at 250° C. (Jensen et al., 1999). However, considerably less hydrogen was released at 100° C. (Jensen et al., 1999). The procedure used by Jensen et al. (1999) to prepare doped sodium alanate involved mechanical ball milling of sodium alanate with liquid Ti- and Zn-alkoxide catalysts. Gross et al. (2000) confirmed that this material could provide cyclic hydrogen storage in larger scale (100 gm) reactors. However, they also suggested that residual oxygen and hydrocarbon impurities resulting from the preparation protocol could result in a much lower than expected hydrogen recharge capacity after the initial cycle of hydrogen discharge. Cyclic capacity of sodium alanate doped with 2 mol % of $Zr(Opr)_4$ and $Ti(OBu^n)_4$ was reported by Gross et al. (2000) to be only about 3 wt. % hydrogen. The kinetics of hydrogen uptake and release were slower than desirable for use in hydrogen powered vehicles, with up to up to 4–5 hours required for hydrogen desorption at 125° C. The results of Gross et al. (2000) suggest that further development of the doped sodium alanate system is needed for practical commercial application.

Additional dopants for dehydriding sodium alanate were investigated by Jensen et al. (in *Proceedings of the DOE Hydrogen Program Review*, NREL/CP-570-39535, 2001). It was reported that $Ti(O^n)Bu)_4$, $\beta$-$TiCl_3$ and $TiCl_4$ gave dehydriding rates of 1.8 wt. % per hour at 100° C., while Zr(O"Pr)$_4$ catalyzed a desorption rate of only 0.6 wt. % per hour. {(C$_5$H$_5$)$_2$ZrH($\mu$-H)$_2$AlH$_2$(NMe$_3$)} and {(C$_3$H$_5$)$_2$TiH ($\mu$-H)$_2$AlH$_2$(THF)} produced dehydriding rates of only 0.2 wt. % per hour. It was concluded that aluminum-transition metal alloys exhibited little or no kinetic enhancement of hydrogen release from doped sodium alanate, while transition metal-aluminum hydride complexes resulted in only modest kinetic enhancement. Although other dopants tested provided better kinetic enhancement of hydrogen release, the wt. % release of hydrogen was still much lower than the DOE guidelines at 100° C. It was concluded that further catalyst development was required in order for these materials to achieve commercial viability (Jensen et al., 2001).

In preferred embodiments of the present invention, sodium alanate is doped with an improved catalyst —{n$^5$-C$_5$H$_5$}$_2$TiH$_2$ (FIG. 1). The use of unsaturated, 5-carbon cyclic ring structures to coordinate the titanium catalyst is advantageous in that it stabilizes the catalyst in the +3 redox state. Ti$^{3+}$ is preferred to Ti$^{4+}$ as a catalyst for sodium alanate hydrogen storage. The use of cyclopentadienyl ring compounds to coordinate with the titanium catalyst provides the advantage of increasing the maximum wt. % of recylcable hydrogen storage compared with other dopants known in the art. In more preferred embodiments of the invention, the cyclopentadienyl rings are removed from the doped sodium alanate by several cycles of hydrogen discharge and recharge (i.e. heating to 100° C.). Compared to non-volatile titanium compounds, such as titanium chlorides, the use of volatile hydrocarbon rings provides substantial weight advantages. It is also advantageous that the compound does not contain any oxygen, like the alkoxide-coordinated transition metal catalysts, as oxygen has been reported to interfere with cyclic discharge and recharge of alanates (Gross et al., 2000).

Although FIG. 1 shows a preferred embodiment of the ring structure as comprising just hydrogen and carbon, it is contemplated within the scope of the invention that virtually any modification and/or substitution could be made in the cyclopentadienyl ring structure, so long as it is still capable of coordinating with and stabilizing Ti$^{3+}$. Such substitutions and/or modifications of cyclopentadienyl rings are known in the art (see, e.g., U.S. Pat. Nos. 5,504,223; 5,703,257; 6,197,990). In alternative embodiments, it is contemplated that six membered carbon rings might also be used to coordinate with the titanium catalyst. In other alternative embodiments, it is contemplated that one or more ring carbons could be substituted with other atoms, such as nitrogen. Various carbon ring substitutions of potential use are known in the art. Preferably, such substitutions and/or modifications of the hydrocarbon ring would not interfere with the removal of the hydrocarbon compound by heating and/or cyclic hydrogen discharge and recharge.

In certain embodiments of the invention, the molar ratios of NaH, aluminum and dopant may be adjusted to provide optimal percent weight hydrogen storage. In an exemplary embodiment the ratios of NaH:aluminum:titanium are 0.7:1.0:0.1. However, molar ratios of NaH may vary between 0.1 to 0.88, while molar ratios of dopant may vary from 0.04 to 0.3. In preferred embodiments, the molar ratio of aluminum added to the compound would be 1.0. Typically, for each mole of dopant added to the compound, one would remove 3 moles of sodium from the composition, since each titanium can coordinate up to three hydrogens. The use of such molar ratios is advantageous in providing the maximum weight percent of hydrogen storage and in optimizing the thermodynamic properties of hydrogen discharge and/or recharge. Another advantage is in increasing the amount of hydrogen available to be released at 100° C.

In other alternative embodiments of the invention, titanium may be replaced with zinc. Other transition metals of potential use as catalysts in place of titanium include Sc, Y, La, Hf, V, Nb, Zr, Ta and/or any of the known lanthanides or actinides. In preferred embodiments, the transition metal would be coordinated with the same type of cyclopentadienyl ring structure disclosed herein to form the initial doped sodium alanate composition.

The components of the doped sodium alanate composition, such as NaH and aluminum may be obtained from commercial sources, for example Sigma/Aldrich Chemicals (St. Louis, Mo.). The dopant, cyclopentadienyl titanium dihydride, may be prepared by a variety of synthetic methods known in the art (see, e.g., Bercaw et al., *J. Am. Chem. Soc.* 94:1219–1238, 1972; U.S. Pat. Nos. 5,104,838; 5,504, 223; 5,703,257; 6,197,990; 6,403,772). Bis(cyclopentadienyl) compounds (also known as metallocenes or "sandwich compounds") have been known for over fifty years. Synthetic routes may start from dicyclopentadiene, which can undergo a reverse Diels-Alder reaction to yield the free cyclopentadiene. Cyclopentadiene may in turn be deprotonated using an alkali metal to produce the cyclopentadienyl compound. Alternatively, cyclopentadiene may be reduced in the presence of titanium to yield the titanium-coordinated bis(cyclopentadienyl) compound (e.g., Whitesides et al., *J. Organometal. Chem.* 92:215, 1975).

Methods of Producing Doped Sodium Alanate

It is contemplated that any known method of preparing doped sodium alanate may be used in the practice of the present invention. These include, but are not limited to, mixing the components in organic solvent followed by vacuum removal of solvent (U.S. Pat. No. 6,106,801), magnetic or other stirring of powdered components (U.S. Pat. No. 6,106,801), and/or ball milling of dry sodium alanate with dry or liquid dopant under argon or another noble gas (e.g., Jensen et al., 1999; Zidan et al., 1999; Gross et al., 2001).

In certain embodiments of the invention, doped sodium alanate may be prepared by brief mixing and melting of the components. For example, NaH, Al and {n$^5$-C$_5$H$_5$}$_2$TiH$_2$ may be mixed together by any known method and the mixture heated to 182° C. or higher. The time of heating is not considered critical, so long as it is sufficient to melt the doped sodium alanate composition. In preferred embodiments, heating is maintained for a time sufficient to drive off the cyclopentadienyl ring component of the mixture. A non-limiting example would be to heat the mixture to between 200 to 250° C. for 5 to 30 minutes. In alternative embodiments, no mixing is involved and the components are added together and heated.

Gross et al. (2000) disclosed the accidental heating of a doped sodium alanate composition above the melting point of the mixture. They reported that the melted doped sodium alanate sintered into a porous solid mass, which did not interfere with hydrogen storage characteristics. However, Gross et al. (2000) used doped sodium alanate that had been initially prepared by ball milling. The instant disclosure is the first report of doped sodium alanate preparation by melting without ball milling. This procedure offers the advantage of eliminating ball milling, which is laborious, tedious and increases the cost and complexity of preparing doped sodium alanate compositions. It was unexpected that melting alone without ball milling or a similar thorough mixing process would be sufficient to form the doped sodium alanate compositions disclosed herein.

Cassette Storage System for Doped Sodium Alanate

Cassette

In certain embodiments of the invention, the doped sodium alanate compositions may be stored, transported and/or used in interchangeable cassette modules. Cassettes may be charged with hydrogen gas under high pressure while attached to a hydrogen utilizing system, such as a vehicle, fuel cell, electrical power unit, catalytic heater and/or hydrogen combustion system. In this case it may be preferred to design the hydrogen utilizing system to include a temperature control module to remove excess heat that is generated during the hydrogen charging process. Alternatively, after being depleted of hydrogen the cassettes may be removed from the hydrogen utilizing system and replaced with charged cassettes, while the depleted cassettes may be recharged in a separate hydrogen charging system. In such embodiments, hydrogen charging may occur at relatively slow rates and low temperatures, eliminating the need for a temperature control module. Where rapid rates of hydrogen charging are preferred, a temperature control module comprising any form of heat transfer device known in the art may be used. Non-limiting examples include fluid or water-filled tubes, water jackets, cooling fins and other radiative devices, heat pumps, fans, etc. Rapid hydrogen charging may also occur at elevated hydrogen pressures.

An exemplary embodiment of a cassette storage system and hydrogen utilizing system suitable for use in the claimed methods and apparatus is disclosed in U.S. patent application Ser. Nos. 10/099,274, filed Mar. 15, 2002, 10/099,771, filed Mar. 15, 2002 and 10/241,125, filed Sep. 10, 2002, the entire contents of which are incorporated herein by reference. Advantages of the cassette system include its safety, ease of use, low cost and transportability. The cassettes are waterproof and gas leak proof. They are resistant to thermal, electrical and mechanical stress, as might occur, for example, in a vehicle collision. During storage and transport, the doped sodium alanate should release only low amounts of hydrogen gas. Thus, the cassettes may be transported with little or no internal gas pressure. Even at an operating temperature of 100° C., the doped sodium alanate composition should not generate more than a few atmospheres of hydrogen gas pressure. Because of the flammable and potentially explosive nature of hydrogen gas, the ability to transport the cassette system with little or no internal pressure is a significant safety advantage.

Figure 2:
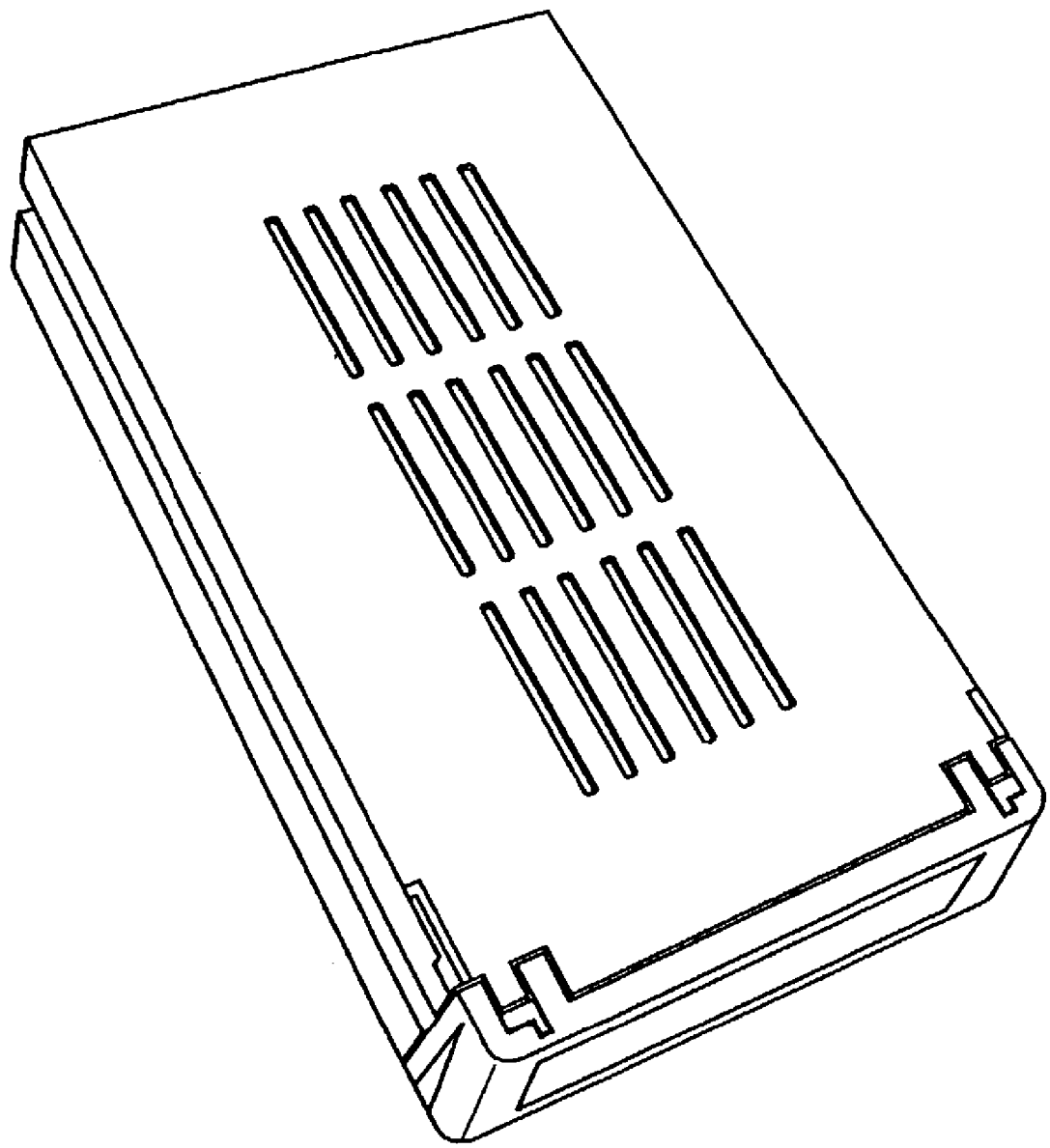
FIG. 2 illustrates an exemplary cassette for storing, transporting and using doped sodium alanate.

A non-limiting example of a cassette is illustrated in FIG. 2. Each A2 size cassette holds a liter of doped alanate composition (FIG. 2). In preferred embodiments, the cassette is configured to fit into a cassette-receiving receptacle of a hydrogen utilizing system (e.g., FIG. 3). The cassette (FIG. 2) may comprise a rigid, impact resistant plastic casing that may have a pivoted handle at one end. Any type of strong, impact, thermal and chemical resistant plastic may be used for the casing, such as polycarbonate, PVP, PTFE, vinyl or acrylic. Other casing materials of use include aluminum, ceramic and/or a composite of aluminum, ceramic and/or plastic. In some embodiments, the cassette may comprise a spring-loaded or other type of door that is pushed open when the cassette is inserted into a cassette receptacle, allowing an inlet/outlet coupling to connect to a hydrogen valve (e.g., FIG. 6) on the cassette. In other embodiments, a metalized paper or plastic covering may be sealed over an aperture in the cassette with adhesive. The user would peel off the sealant before inserting the cassette into the receptacle. Flanges on the cassette housing may be used to align the cassette with the receptacle and inlet/outlet coupling. In various embodiments, it is contemplated that any hydrogen valves (e.g., FIG. 6) would be located on the side of the cassette that is pushed into the receptacle and mating with the coupling would occur automatically when the cassette is firmly seated in the receptacle. In alternative embodiments of the invention, the hydrogen valve(s) may be located on the side of the cassette facing away from the receptacle and the user may manually attach one or more couplings to the valve(s).

In addition to a thermoplastic outer cover, the doped sodium alanate may be further enclosed in one or more layers of other material to provide additional protection against puncture and/or exposure of the alanate to the environment. Exposure of sodium alanate to water, for example, could result in rapid release of hydrogen that may form an explosive mixture with air. Materials that may be used as additional sealing layers include, but are not limited to, a flexible metalized fabric, Mylar, plastic/foil, Kevlar™, SpectraFabric™ antiballistic woven mesh fabric or similar robust yet lightweight thin skin or sheath housing. The use of flexible materials for the additional layers is preferred, as impact with a pointed object would be less likely to puncture a material that can deform.

Hydrogen Valve

Figure 6:
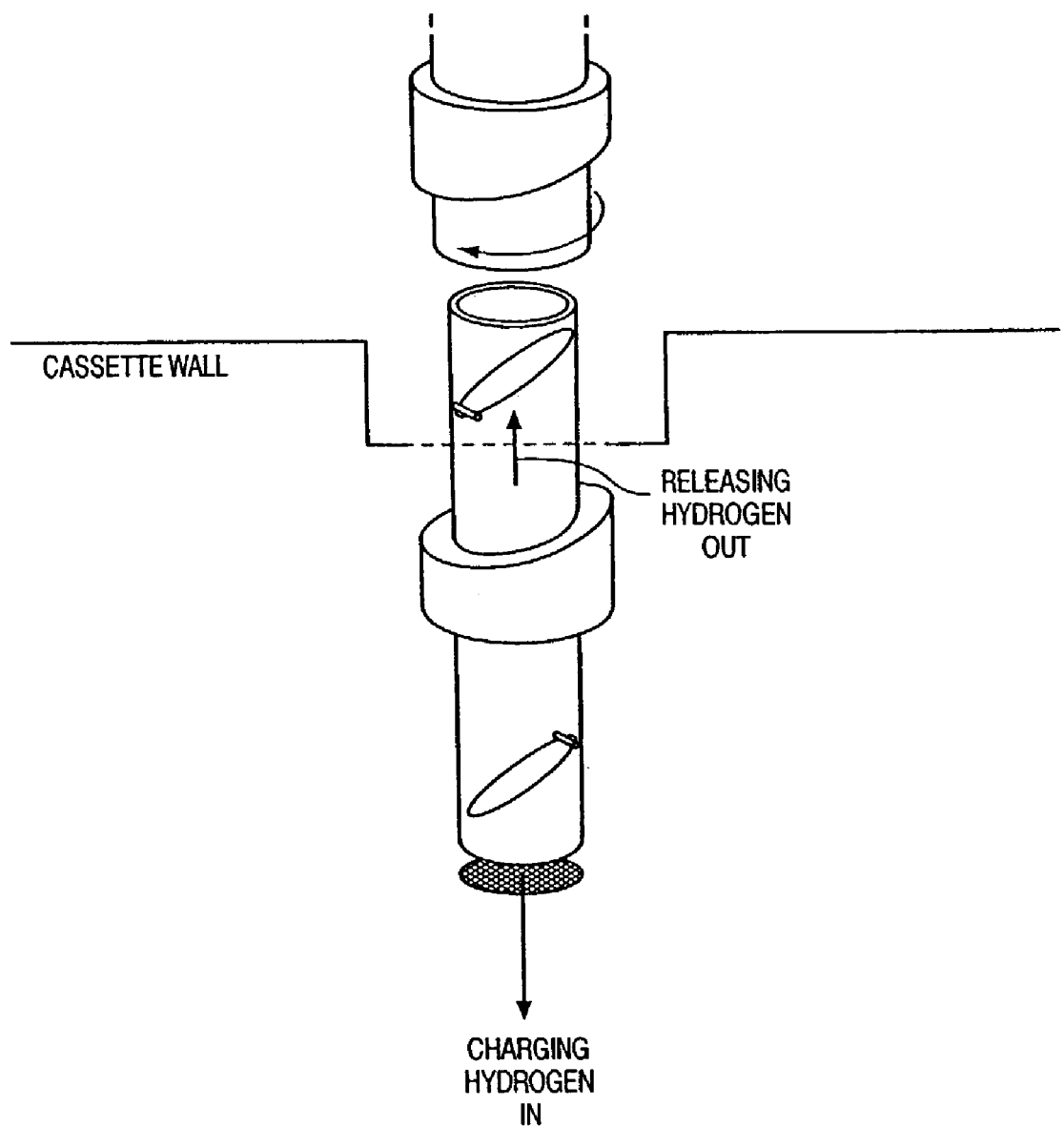
FIG. 6 illustrates an exemplary embodiment of a hydrogen valve.

In certain embodiments of the invention, the cassette may comprise one or more hydrogen valves (e.g., FIG. 6). The valve would normally be in a closed position, preventing entrance or exit of any material. In preferred embodiments, when the valve is open it only allows passage of hydrogen gas and would exclude, for example, passage of water. The valve may open, for example, in response to the generation of about 1 atmosphere of hydrogen gas pressure inside the cassette. Alternatively, the valve may open, for example, in response to the application of two or more atmospheres of hydrogen gas pressure outside the cassette. Those pressures are not limiting and other pressure set points may be used. Thus, in some embodiments the valve is a two-way valve that will allow hydrogen to leave or enter the cassette. In alternative embodiments, the cassette may comprise two one-way valves, a first valve that opens only in response to hydrogen pressure inside the cassette and a second valve that opens only in response to elevated pressure from a hydrogen charging system outside the cassette. In the most preferred embodiments, the valve(s) will not allow passage of liquids, only of gas.

It is contemplated within the scope of the invention that any known method of opening and closing the valve(s) may be utilized. Thus, valve opening could occur automatically in response to pressure gradients. Alternatively, electrically controlled valves, such as solenoid operated valves, could open and close in response to signals from an information processing and control system. In some embodiments of the invention, disclosed in more detail in the Examples below, the valve is a bi-directional one-way valve (FIG. 6). When in one configuration, the valve allows hydrogen to flow from the inside of the cassette to the outside, while in an alternative configuration the valve allows hydrogen to flow from the outside of the cassette to the inside, as in hydrogen recharging of the cassette.

Exemplary valves suitable for use are known for controlling gas flow in the nuclear power industry. The gate type design uses spring loaded seal discs that seal tightly at all pressures from 0 psig to maximum rating. When open, the valve permits bi-directional flow with tight sealing in both flow directions. Because of the straight-through flow path with self-cleaning sealing surfaces, internal passages inherently resist any buildup of contamination. Features may include zero leakage to the environment; the absence of any packings, bellows, or diaphragms; a valve rating of ANSI class 150 to 2500; high cycle life with over 100,000 operations in most applications; straight-through flow; and resistance to contamination build-up. The valve body material may comprise stainless steel, carbon steel, AL6V or other ASME Materials. The seats may be carbon. In certain embodiments, position indication switches are available for remote status indication. The valve may comprise socket weld, butt weld or tube extension line connections. Opening and closing of the valve may be controlled by a solenoid operator, constructed of Class H or better materials. Solenoid and switch assemblies may be accessible for removal or maintenance without disturbing the pressure boundary.

Another exemplary valve that may be of use is the latex-free Carhill Valve System designed for use in artificial resuscitation (CORPAK, Wheeling, Ill.). A silicone duckbill valve allows the one-way passage of air. A 99% BFE bi-directional filter prevents cross-contamination of the doped sodium alanate composition.

In another exemplary embodiment, Quick-Connecting Fluid Couplers provide connections in systems that involve the flow of air or gas (Nitto Kohki, Hanover Park, Ill.). A built in automatic open and shut valve provides high flow, easy flow control and an excellent seal. Available valves include Pneumatic HI-CUPLA, Plastic HI-CUPLA ACE, Semiconductor Semicon Cupla, Ultra Small Micro Coupler and Full Blow Cupla. The valve(s) of use in the embodiments are not limited to the examples disclosed herein but may include any valve known in the art that will allow passage of hydrogen gas without leakage of sodium alanate. Preferably, the valve(s) will also prevent atmospheric oxygen and/or external water from contaminating the doped sodium alanate.

Smart Chip

In some embodiments of the invention, a smart chip may be incorporated into the cassette housing or placed inside the cassette, for example in contact with the doped sodium alanate. An exemplary embodiment of a smart chip would be a flash memory chip as used in digital cameras, computer BIOS chips, CompactFlash, SmartMedia, Memory Stick, PCMCIA Type I and Type II memory cards and memory cards for video game consoles. Flash memory is considered to be a solid state memory device, since it has no moving parts. Flash memory chips may be obtained from a variety of commercial sources, such as 3COM, AVL Technologies Corp., Hewlett-Packard, Hitachi, IBM Corp., NEC, Samsung Corp. and many others. The chip may broadcast a signal that provides information about the cassette operating characteristics to an information processing and control system, such as a computer or microprocessor. Alternatively, the chip may be directly connected via wires or other electrical contacts to an information processing and control system and/or a transmitter. Information to be provided may include such things as the temperature, hydrogen gas pressure and amount of remaining hydrogen charge in the cassette.

The chip may also signal an operator or an external ordering system when it is time to replace a cassette. In some embodiments where more than one cassette is stored or attached to the hydrogen utilizing system, the smart chip may signal the system to automatically switch or replace a depleted cassette with a charged one. The smart chip may be used as part of a control system to regulate hydrogen generation. For example, the information processing and control system may monitor the hydrogen utilizing system to constantly determine the hydrogen needs of the system. The control system may then regulate the rate of hydrogen release, for example by controlling the degree of heating of the alanate composition as discussed below. A feedback system may continually monitor hydrogen pressure inside the cassette and regulate the amount of heat provided to the doped sodium alanate composition, thus regulating temperature and hydrogen release.

Hydrogen Release

Hydrogen may be released from doped sodium alanate by heating, preferably to 100° C. although in certain embodiments hydrogen release at lower temperatures may be sufficient to satisfy power requirements. In some embodiments, the system may include an accessory bottle of hydrogen to fuel the system and initiate power generation, for example from a fuel cell. The electrical power produced may then be used with an electrical heating element, such as a resistive electrical heater, to raise the internal cassette temperature to the operating temperature. In other embodiments, hydrogen from an accessory bottle or from the cassette may directly power a catalytic heater, as discussed below. Alternatively, the hydrogen utilization system may comprise an accessory battery or other power source to provide for initial heating of the cassette. Once hydrogen release has been initiated, the power generated by the hydrogen utilizing system may be used for further heating of the cassette. In some embodiments of the invention a heating element may be incorporated into the cassette itself. In alternative embodiments the heating element is built into the hydrogen utilizing system (e.g, FIG. 4). For example, a retractable heating element may be inserted into the cassette after it has been placed in a cassette receptacle. Any source of heat and any apparatus for heating known in the art may be used to raise the temperature of the alanate composition, including without limitation heat generated by a fuel cell, such as a PEM fuel cell.

Shipping, Ordering and/or Distribution System

In certain embodiments of the invention, cassettes charged with hydrogen may be shipped to any site of utilization, using standard shipping methods and commercial services such as Federal Express, U.S. Postal Service and/or United Parcel Service. A system for ordering, distributing and shipping charged cassettes and returning depleted cassettes is disclosed in U.S. patent application Ser. Nos. 10/099,274, filed Mar. 15, 2002, 10/099,771, filed Mar. 15, 2002 and 10/241,125, filed Sep. 10, 2002. The distribution method is not limiting and any method of providing charged cassettes may be used. In alternative embodiments, charged cassettes may be obtained, for example, at existing service stations, specialized hydrogen refueling stations, distribution centers and/or commercial wholesale or retail outlets. In certain embodiments, disposable cassettes may be designed for single-use applications, for example military field use. In such embodiments, it may be preferred to use materials that will degrade over time, such as biodegradable plastics or equivalent materials. The cassette embodiment is not limiting and it is contemplated that any known system for containing and transporting a solid, hydrogen-generating composition, such as a metal hydride and/or an alanate, may be used with the disclosed doped sodium alanate compositions.

Hydrogen Use

In a cassette embodiment or any other embodiment, the doped sodium alanate compositions may be used to generate hydrogen for any type of known hydrogen utilizing system. In certain embodiments, such a hydrogen utilizing system may comprise a fuel cell. A variety of hydrogen utilizing fuel cell designs are known in the art, including but not limited to the polymer electrolyte membrane (PEM) fuel cell, the phosphoric acid fuel cell, the molten carbonate fuel cell and the solid oxide fuel cell. Alternatively, the doped sodium alanate composition may be used to generate hydrogen to fuel a hydrogen-powered vehicle. Non-limiting examples of known hydrogen-powered vehicles include the Mazda HRX-2 and MX-5 and the BMW 750hL. Other hydrogen-powered vehicles are being developed or tested by most of the major automobile manufacturers, including General Motors, Daimler-Benz, Ford, Toyota and Honda. Conventional ICE vehicles may also be retrofitted to burn hydrogen instead of gasoline. (E.g., U.S. patent application Ser. No. 10/178,974, entitled "Methods and Apparatus for Converting Internal Combustion Engine (ICE) Vehicles to Hydrogen Fuel," by Scott D. Redmond, filed Jun. 25, 2002, the entire text of which is incorporated herein by reference. See also, Quantum Impco-Gaseous Fuel Metering System, Quantum Technologies, Inc., Irvine Calif.). In other embodiments of the invention, hydrogen may be combusted to generate heat and/or electricity, using any combustion system known in the art. Alternatively, the doped sodium alanate composition may be incorporated into power cells to provide energy for portable electronic devices, such as laptop computers, cellular telephones, hearing aids, personal organizers and other portable devices.

Heaters

In various embodiments of the invention, part or all of the hydrogen generated from the alanate composition could be provided to a catalytic hydrogen-powered heater. For example, part of the hydrogen generated could be used to heat the cassette in order to release further hydrogen. Alternatively, a catalytic heater could be incorporated into a hydrogen-powered vehicle to heat the passenger compartment. Any known type of catalytic heater capable of using hydrogen may be used. Catalytic heaters may be obtained from commercial sources, such as Bruest Catalytic Heaters (Branford, Conn.). Catalytic heaters oxidize hydrogen flamelessly, emitting medium to long wave infrared energy. A platinum catalyst forces combustion below the gas ignition point and is capable of generating surface temperatures of up to 1000° F. The temperature is proportional to the rate of reaction, which is in turn dependent on the rate at which hydrogen is provided to the heater. In embodiments involving cassette heating, the rate of hydrogen flow is preferably regulated to maintain the cassette temperature at 100° C. or less.

Other exemplary heaters are available from JP Technologies, Inc. (Raleigh, N.C.). Miniature resistance heaters and Resistance Temperature Detectors (RTD's) are fabricated from thin metallic foils and laminated to thin, heat-resistant plastic substrates. Metal foil may comprise nickel, platinum and/or Balco, with backings and/or encapsulants of Kapton®, glass/epoxy or Mylar. These devices are capable of being bonded onto a variety of intricate shapes, such as the inside or outside surface of cassettes. RTD's may be used in place of or in addition to smart chips to monitor cassette temperature. JP Technologies manufactures thin, metal foil sensors designed for rapid response temperature measurements. The foils used are typically >0.0002" (0.005 mm) thick and have extremely low thermal inertia. In comparison with standard wire wound RTD's, foil RTD's provide maximum surface exposure and make more intimate contact with surfaces. Heaters and RTD's may be integrated onto a common backing material as one heating and temperature measurement unit.

Another exemplary heater that may be used is made by Hytek (Carson City, Nev.). The HY7110 is a miniature proportionally controlled DC heater with integral thermistor and temperature control circuit. Using an 8–35 volt power supply, the heater is programmable and has a single external resistor for precision microheating applications. The HY7115 heater operates on 3–8 volts of power and is programmable, with a single external resistor for precision microheating.

Alternative Hydrogen Storage Compositions

In alternative embodiments of the invention, the disclosed cassette and hydrogen utilizing systems may be employed with hydrogen storage compositions other than doped sodium alanate. Any known hydrogen storage composition may potentially be used. Non-limiting examples include metal hydrides, borohydride (e.g., sodium borohydride or lithium borohydride) solutions exposed to a catalyst such as platinum and solid hydrides exposed to water at elevated temperature. Hydrogen may also be generated by partial oxidation (POX) reformation of natural gas, methane or other hydrocarbons or by catalytic dehydrogenation of hydrocarbons.

Metal hydride compositions for hydrogen storage are well known in the art (e.g., U.S. Pat. Nos. 4,211,537; 4,728,580; 4,667,185; 6,165,643). Systems for hydrogen generation using metal hydride or metal alloy hydrides are also well known (U.S. Pat. Nos. 4,302,217; 4,537,761; 4,570,446; 4,599,867; 5,360,461; 5,797,269; 5,962,155; 5,987,895; 6,143,052; 6,194,092; 6,267,229). Metal hydrides reversibly take up hydrogen gas when exposed to very high pressures of hydrogen. Hydrogen release is facilitated by heating the metal hydride to high temperature.

Hydrogen generating borohydrides, such as lithium or sodium borohydride, are known in the art (see, e.g., U.S. Pat. Nos. 4,000,003; 4,002,726; 4,628,010; 5,372,617). In the presence of an appropriate catalyst, such as platinum, borohydride reacts with water to generate hydrogen and borate. In certain embodiments of the invention, the rate of hydrogen production may be controlled by regulating exposure of the catalyst to the borohydride solution.

In alternative embodiments of the invention, solid chemical hydrides such as lithium borohydride, sodium borohydride, calcium hydride, lithium aluminum hydride or lithium hydride may be used to generate hydrogen upon exposure to water (U.S. Pat. Nos. 4,000,003; 5,372,617; 5,702,491). Another exemplary embodiment is disclosed in U.S. Pat. No. 6,274,093, comprising a compound such as ammonia that can react with a solid compound, such as lithium aluminum tetrahydride, to release hydrogen.

In another exemplary embodiment, hydrogen may be stored in carbon nanotubes and/or fullerenes (e.g., Dillon et al., "Carbon Nanotube Materials for Hydrogen Storage," Proceedings of the 2001 DOE Hydrogen Program Review, http://www.eren.doe.gov/hydrogen/pdfs/30535am.pdf). Methods for preparing carbon nanotubes are known (e.g., U.S. Pat. Nos. 6,258,401; 6,283,812; 6,297,592). Carbon nanotubes may also be obtained from commercial sources, such as CarboLex (Lexington, Ky.), NanoLab (Watertown, Mass.), Materials and Electrochemical Research (Tucson, Ariz.) or Carbon Nano Technologies Inc. (Houston, Tex.).

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Process for Making Doped Sodium Alanate

Sodium hydride and aluminum are obtained from Sigma/Aldrich Chemicals (St. Louis, Mo.). Bis(cyclopentadienyl) titanium dihydride (FIG. 1) is synthesized from dicyclopentadiene, which is heated to undergo a reverse Diels-Alder reaction. The resulting cyclopentadiene is reduced in the presence of titanium to yield bis(cyclopentadienyl) titanium dihydride (e.g., Whitesides et al., 1975). Alternatively, bis (cyclopentadienyl) titanium dihydride is prepared by the method of Bercaw et al. (1972). The components are added together in a molar ratio of 0.7 NaH to 1.0 aluminum to 0.1 bis(cyclopentadienyl) titanium dihydride. After brief mixing by magnetic stirring, the composition is packed into a container (e.g., cassette module) and heated to 190° C. for 30 min. The resulting porous sintered composition is used without further modification. The heating drives off the cyclopentadienyl component, leaving sodium, aluminum, titanium and hydrogen in the resulting composition.

Example 2

Cassette Module

FIG. 2 shows an exemplary embodiment of a cassette module (Hfuel™ A2 cassette) of use in the disclosed apparatus, methods and compositions. The cassette comprises an outer surface of electrically and thermally insulative, impact and chemical resistant plastic, with a single internal compartment holding about 1 liter of doped sodium alanate composition. In alternative embodiments, the outer casing is comprised of aluminum, ceramic, or an aluminum/ceramic composite. The alanate composition is surrounded by a series of layered materials, comprising an inner layer of flexible metalized plastic, a middle layer of Kevlar™, and an outer layer of Mylar, surrounded by a small gas (air) space and the outer rigid plastic cover. A hinged handle for inserting and removing the module from a hydrogen utilizing system is present at one end of the cassette. The other end of the cassette interfaces with the hydrogen utilizing system. In preferred embodiments, there is a single opening between the alanate composition and the outside of the cassette, consisting of a bidirectional, one-way valve for hydrogen movement (discussed below). When the cassette is inserted into a hydrogen utilizing system or a hydrogen charging system, the valve mates with a coupling on the system.

In preferred embodiments, the cassette also contains a smart chip that may be in contact with the alanate composition, or may be located between the rigid cover and one or more of the insulating layers discussed above. The smart chip may detect and report conditions inside the cassette to an external information processing and control system. Preferably, the chip may monitor and report such conditions as the temperature of the cassette contents, the hydrogen gas pressure inside the cassette and the amount of hydrogen charge remaining in the cassette. In some embodiments, the smart chip may be part of a feedback control system that monitors the hydrogen gas requirements of the hydrogen utilizing system and the temperature and pressure inside the cassette. For example, an increase in hydrogen demand may result in an increase in heat provided to the cassette contents, resulting in an elevated temperature of the alanate composition and increased release of hydrogen gas. Depletion of hydrogen fuel from a cassette may result in a signal to an operator to replace or recharge the cassette, or may alternatively result in a signal to an external ordering and delivery system to send a replacement cassette. In other alternative embodiments, a depleted cassette may automatically be replaced with a charged cassette in systems with multiple cassettes. Preferably, the smart chip contains an integrated radiofrequency transmitter that sends information to the information processing and control system without direct electrical connections. Alternatively, the cassette module may contain one or more electrical leads that attach the smart chip and any other internal electrical components (e.g., electrical heating element) to an electrical connector on the hydrogen utilizing system.

Example 3

Hydrogen Utilizing System

Figure 3:
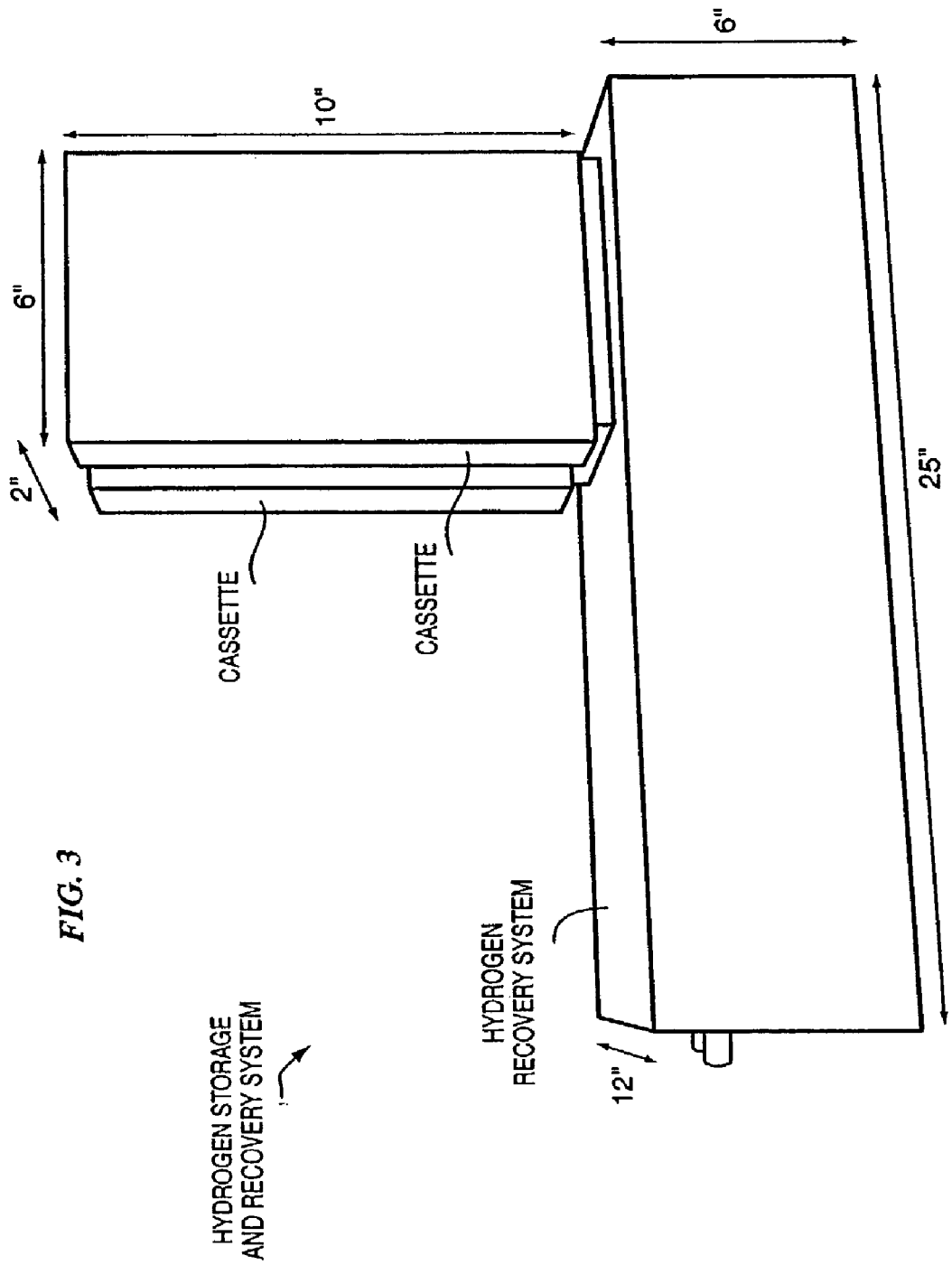
FIG. 3 illustrates an exemplary hydrogen utilizing system.

In preferred embodiments, the cassette is designed as a modular unit to be inserted into a hydrogen utilizing system. An exemplary embodiment of a hydrogen utilizing system is illustrated in FIG. 3. As indicated, the cassette modules plug into a hydrogen utilizing system (Decom™ unit). In this illustrative embodiment, two Hfuel™ cassettes are inserted into a Decom™ system. The Decom™ system may be designed as a fully self-contained electrical power generator, feeding hydrogen gas generated by the cassettes to an internal fuel cell that may generate 6 or 12 volt direct current (DC) electrical power. In certain embodiments, the Decom™ unit may also comprise, or be attached to, an AC/DC converter that can provide 120 volt AC power to electrical devices. In other embodiments, the Decom™ unit may feed hydrogen gas to a combustion system, such as an ICE vehicle. In the exemplary embodiment shown in FIG. 3, the Decom™ unit is about 12" deep, 6" tall and 25" wide, while the cassettes are about 2" deep, 6" wide and 10" tall. The skilled artisan will realize that in different embodiments the cassettes may be smaller or larger in size, to accommodate interfacing with various hydrogen utilizing systems.

Example 4

Components of Hydrogen Utilizing System

Figure 5:
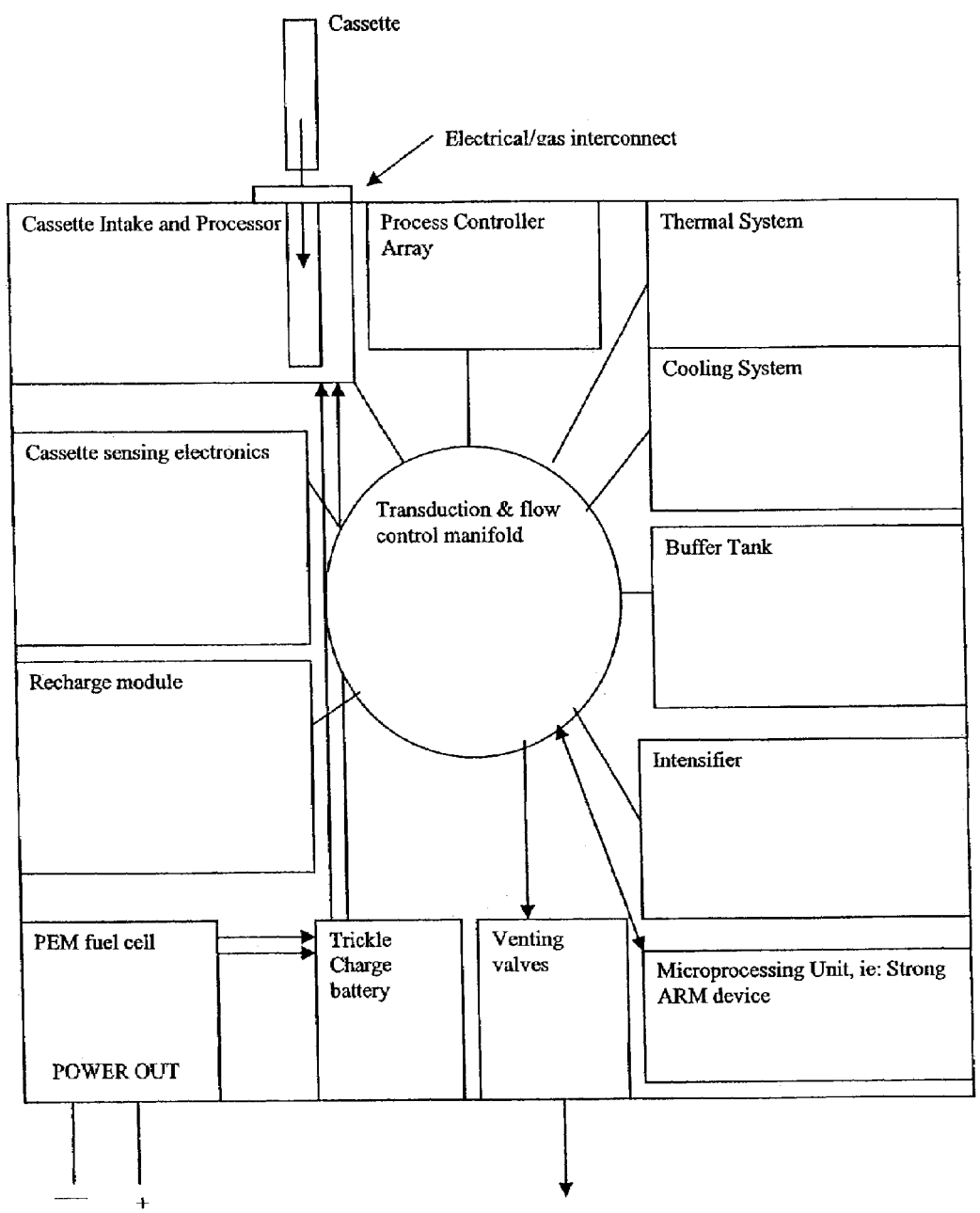
FIG. 5 shows a schematic diagram of an exemplary hydrogen utilizing system.

A schematic diagram showing the components of an exemplary hydrogen utilizing system (Decom™ unit) is provided in FIG. 5. A cassette is inserted into a cassette intake and processor element. A cassette sensing module may be internal (e.g., smart chip) or external to the cassette. Hydrogen may be provided to a variety of hydrogen utilizing elements, such as a PEM fuel cell. The fuel cell utilizes hydrogen and oxygen (or air) to generate electrical power.

In certain embodiments, a recharge module may be present that recharges the cassette in place by providing hydrogen gas under high pressure. Alternatively, cassettes may simply be removed and replaced with fresh cassettes. Thus, the recharge module may be an optional component of the system. Where cassettes are recharged while attached to the system, the cassette may generate excess heat. The PEM fuel cell may also generate heat during operation. Thus, a cooling system may be present to remove excess heat from the system. Release of hydrogen from the alanate composition requires heating of the composition. In alternative embodiments, electrical heating elements may be built into the cassette (for example, HY7110 or HY7115 DC heaters from Hytek, Carson City, Nev.). In such case, electrical leads may be provided from the fuel cell and/or a trickle charge backup battery to heat the cassette. Alternatively, heating elements contained within the Decom™ unit may be inserted into the cassette to provide heat. In this case, the hydrogen utilizing system may alternatively comprise a thermal module. A backup hydrogen storage tank (buffer tank) may also be included to provide a hydrogen supply to the fuel cell or other hydrogen utilizing elements while the alanate composition is being heated. In certain embodiments, one or more venting valves may be included to release excessive hydrogen pressure from the system.

In certain embodiments, the hydrogen utilizing system may comprise an intensifier element. An intensifier may, for example, generate infrared, laser, ultrasonic, vibration, microwave, terrahertz or other electromagnetic frequency radiation to speed up, slow down or otherwise alter the kinetics of hydrogen absorption or release or other processes within the Decom™ unit. The various processes occurring within the Decom™ unit may be integrated through a transduction and flow control manifold coupled to a process controller array. In various embodiments, the functions of the hydrogen utilizing system may be regulated by an information processing and control system (microprocessing unit, for example a Strong ARM device, Digi-Key, Thief River Falls, Minn.). The skilled artisan will realize that the disclosed embodiment is illustrative only and that other hydrogen utilizing systems, comprising some or all of the elements discussed above and/or comprising additional elements that are known in the art may be used in the claimed methods, apparatus and compositions.

Example 5

Cassette Heaters

Alternative exemplary embodiments of a cassette heating system are illustrated in FIG. 4. In certain embodiments (FIG. 4A, FIG. 4B), the heating elements are part of the hydrogen utilizing system and are inserted into spaces within the cassette module. In other embodiments (FIG. 4C, FIG. 4D) the heating elements may be incorporated into the cassette itself or may transfer heat through elements that are external to the cassette housing when in use.

Figure 4B:
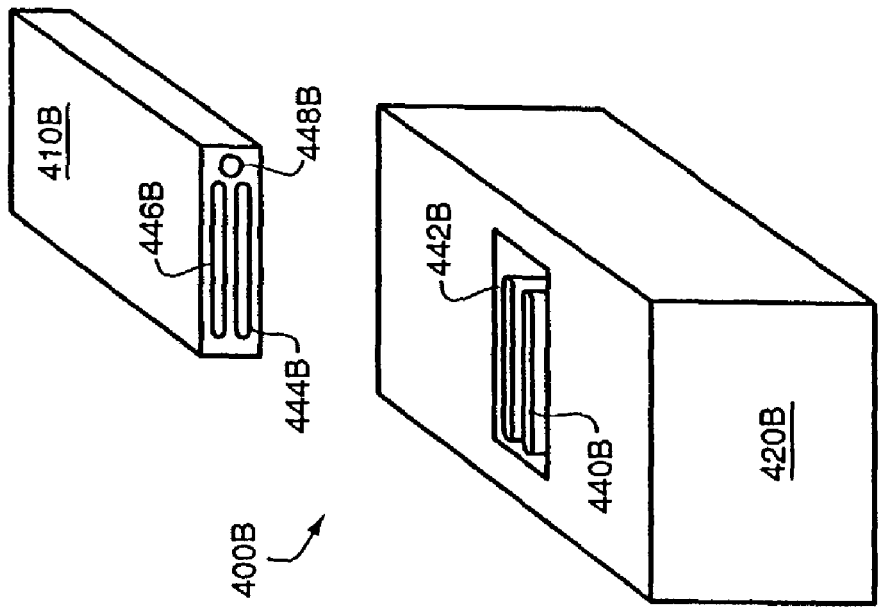
FIG. 4B shows another exemplary embodiment of a cassette heating system.
Figure 4A:
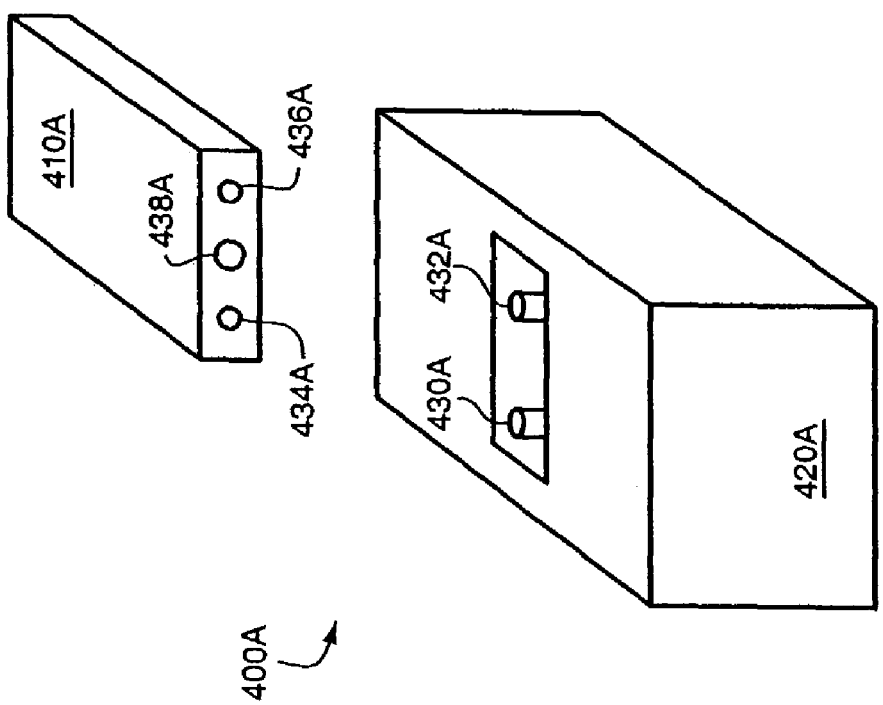
FIG. 4A shows an exemplary embodiment of a cassette heating system.

FIG. 4A shows an embodiment where heating elements in the form of thermal prongs 430A, 432A of a hydrogen recovery system 420A are inserted into corresponding holes 434A, 436A in the base of a cassette 410A. Hydrogen is recovered through a valve 438A. FIG. 4B shows an embodiment where heating elements in the form of thermal vanes 440B, 442B of a hydrogen recovery system 420B are inserted into corresponding slots 444B, 446B in a cassette 410B. Hydrogen is recovered through a valve 448B. The prongs or vanes may extend through most of the length of the cassettes, for example between about 50–100% the length of the cassette, in order to obtain good distribution of heat to alanate composition at the back of the cassette.

In either embodiment (FIG. 4A, FIG. 4B), heat may be generated by any method known in the art, such as electrical resistive heaters that are contained within or that are thermally coupled with the respective prongs or vanes. The heat may also be generated by catalytic oxidation of hydrogen, or otherwise, and conveyed to the thermal elements. In certain embodiments, heat generated by a PEM or other fuel cell may be used to heat the contents of the cassette. In embodiments wherein heat is received from an inserted thermal element (FIG. 4A, FIG. 4B), thermal insulation would typically not be disposed between the inserted heating element and the hydrogen storing material. Similarly, there may be minimal or no gas or air space between the heating element and the doped sodium alanate in order to allow good conduction. The heat provided by the heating elements may increase the temperature of the alanate composition, causing release and recovery of hydrogen, and causing the hydrogen to exit the cassettes through the openings and valves. In an alternate embodiment of the invention, thermal prongs, thermal vanes, or other heating elements may be formed within the cassette and may receive heat or electrical current sufficient to cause resistive heating within the elements from an external source.

Figure 4D:
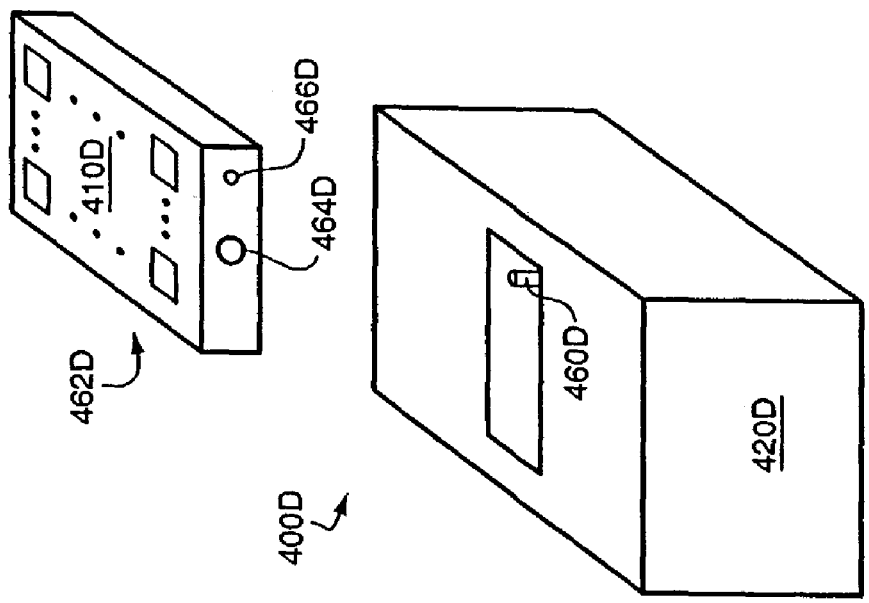
FIG. 4D shows another exemplary embodiment of a cassette heating system.
Figure 4C:
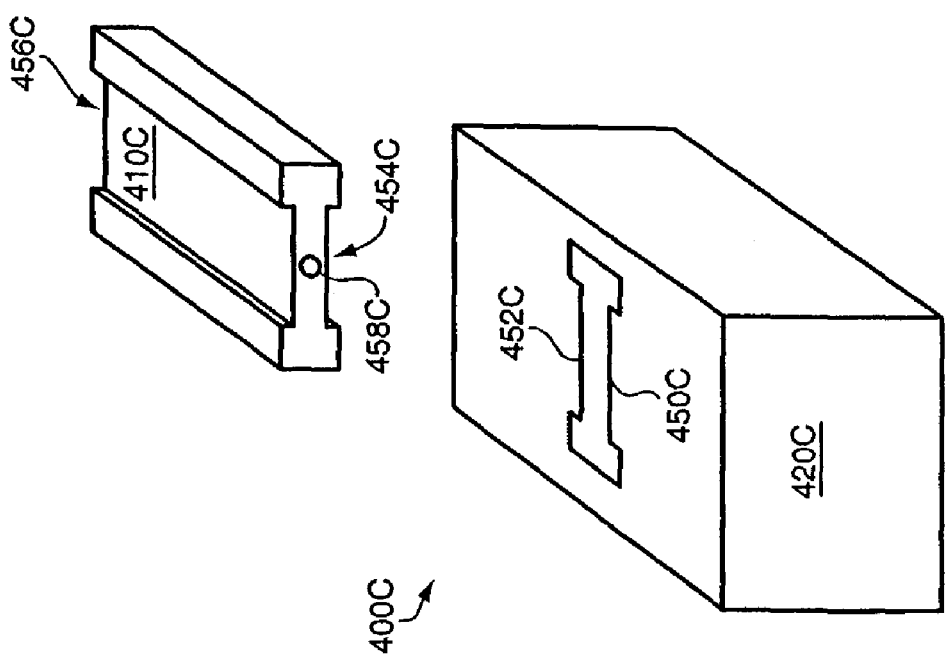
FIG. 4C shows another exemplary embodiment of a cassette heating system.

FIG. 4C shows another exemplary heating system for heating a cassette 410C in a hydrogen recovery system 420C wherein a portion of the exterior of the cassette is sufficiently conductive to allow influx of externally supplied heat. The particular cassette 410C illustrated has thermal conduction recesses 454C, 456C or grooves that run along its top and bottom surfaces. The recesses may directly couple with and contact mating thermal ridges or ribs 450C, 452C that protrude from the hydrogen recovery system and that are connected with the thermal system to provide heat to the cassette through the recesses. Hydrogen recovered by heating may exit though an opening regulated by a valve 458C. In contrast to the rest of the cassette outer covering, the thermal conduction recesses may contain thermally conductive materials in order to facilitate heat transfer from the thermal ribs to the hydrogen storing material within the cassette. The portions of the cassette housing making up the surfaces of the recess would often not contain an insulating material or layer. In some embodiments, the cassette may contain internal heat transfer elements, such as vanes, tubes, or fins, which may thermally couple with the thermal conduction recesses and help to conduct and distribute heat to the material within the cassette.

In some embodiments of the invention, removable protective covers, potentially containing an insulating material, may be inserted into the thermal conduction recesses 454C, 456C, for example by sliding into grooves or other couplings on the sidewalls of the recesses, in order to protect the alanate composition and potentially reduce thermal influx during shipping, and at other times when the cassette is not inserted into the hydrogen recovery system for hydrogen recovery. Of course, the thermal conduction recesses are not required, and in an alternate embodiment of the invention a non-recessed portion of the housing of a cassette may contain a conductive material and lack thermal insulation to allow influx of externally applied heat.

FIG. 4D shows an exemplary heating system for heating a cassette 410D in a hydrogen recovery system 420D containing a plurality of resistive heaters 462D (any desired number) as heating elements in order to recover hydrogen through an opening regulated by a valve 464D. The resistive heaters may be incorporated into the cassette housing or contained within the cassette interior, for example distributed around the cassette interior to distribute heat efficiently to the doped alanate. Examples of resistive heaters include but are not limited to Thermofoil™ combined resistance heaters and sensors available from Minco Products, Inc. of Minneapolis, Minn., HY-7110 and HY-7115 heaters available from Hytek Microsystems of Carson City, Nev., and miniature resistance heaters available from Vishay Intertechnology, Inc. of Malvern, Pa. The cassette may contain an electrical outlet 466D or other receptacle or contact for a plug 460D of the recovery system to receive electrical current to cause heating within the resistive heaters. The resistance heaters may receive electrical current, either direct or alternating current, from an external power source. The external power source may be within the hydrogen recovery system (e.g., a trickle charge battery or an internal fuel cell), may be within a hydrogen utilization system (e.g., a fuel cell or a battery of a vehicle), or may be from another source (e.g., a power outlet). In yet another embodiment, thermal tubes, panels, vanes or rods may be built into the cassette so that if power or heat is passed to them from an external source they may heat the cassette contents.

Example 6

Hydrogen Valve

An exemplary embodiment of a hydrogen valve of use in the disclosed apparatus and methods is shown in FIG. 6. The valve is a switchable bi-directional one way valve. When the valve is switched in one direction, it allows hydrogen gas to pass from the cassette module to a hydrogen utilizing system. When the valve is switched in the other direction, it allows the cassette to be charged with pressurized hydrogen gas from an external supply. In either switching mode, gas may flow in one direction only. The valve is designed to allow movement of gas, but to prevent the movement of water or other liquids. A variety of water impermeable gas valves are known in the art. For example, such a valve might comprise a selectively permeable membrane that allows passage of gas but not water, for example a GORE-TEX® (W.L. Gore and Associates, Inc., Newark, Del.) or other membrane.

In preferred embodiments, the valve direction is determined by the coupling to which it is attached. When the cassette is inserted into a hydrogen utilizing system, the coupling turns a collar that allows hydrogen gas to exit the cassette. When the cassette is attached to a hydrogen charging system, the coupling switches the valve to the other direction, allowing hydrogen gas to enter the cassette and recharge the alanate composition. Various embodiments may utilize different mechanisms, such as a male to female or female to male connection or a locking collar that can slide up or down, depending on the coupling attachment. Alternatively, the locking collar may be fixed in one position or another by a surface mount.

Example 7

Method for Ordering, Distributing and Shipping Cassettes

Figure 7:
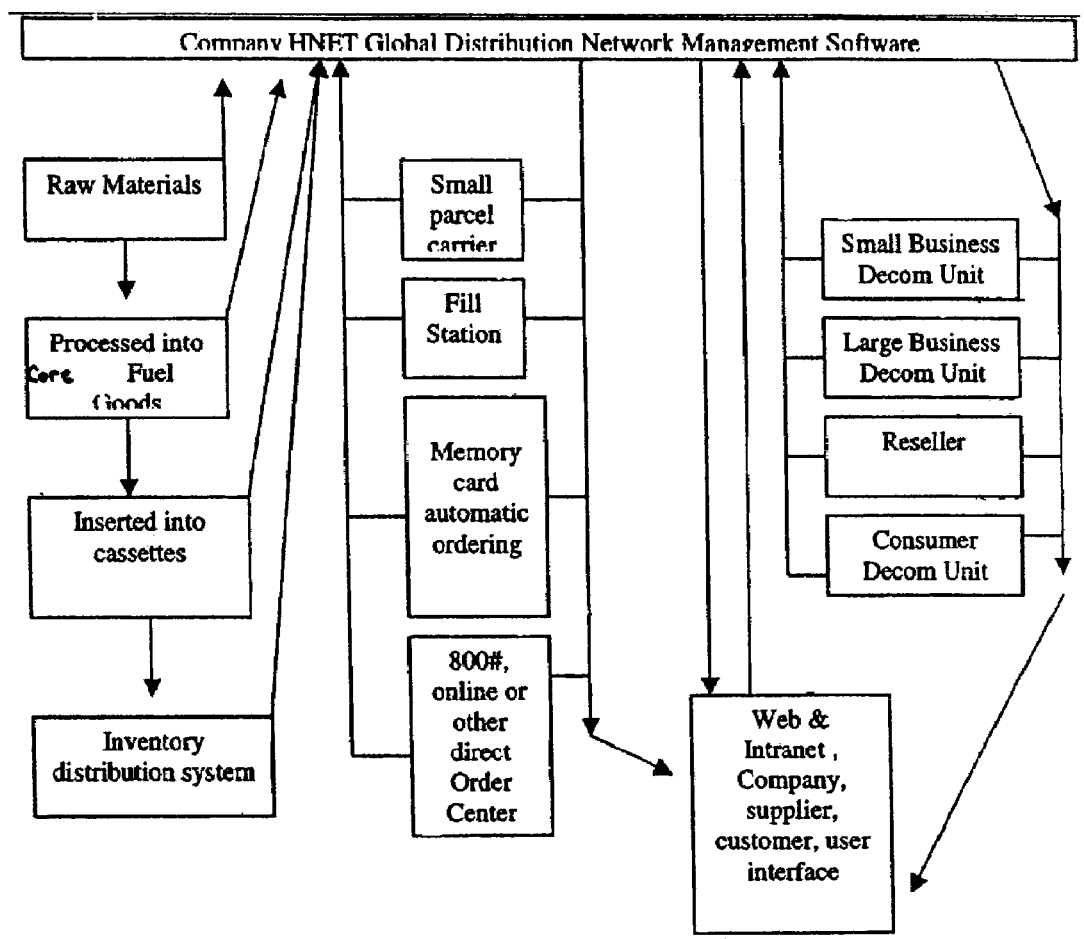
FIG. 7 shows an exemplary embodiment of a method for ordering, distributing and/or shipping hydrogen charged cassettes.

FIG. 7 illustrates an exemplary system for ordering, distributing and shipping charged cassettes and recovering discharged cassettes, for embodiments wherein the discharged cassettes are not recharged while they are attached to a hydrogen utilizing system. For example, cassettes may be used in remote locations where there is no available high-pressure hydrogen gas source. In such case, it may be preferred to ship fully charged cassettes to the remote location and to return discharged cassettes to a central facility. As indicated in FIG. 7, an H-Net™ Global Distribution Network Management Software system may control one or more aspects of cassette distribution. In certain embodiments, a smart chip or other monitoring device inserted into or attached to a cassette may detect the discharge status of the cassette. When the cassette reaches a predetermined level of remaining hydrogen charge, the smart chip may signal the Management system to ship a replacement cassette to the use location. The Management system may interface with an inventory distribution system to place an order for one or more cassettes. The Management system may also place an order for pickup and shipment of replacement cassette(s) with a small parcel carrier. The delivery of the replacement cassette(s) may also be monitored by the Management system.

The H-Net™ global distribution network management software system may receive input from a variety of sources, such as information related to the fabrication or creation of new sets of each fuel cassettes. Information related to raw materials and the fabrication of raw materials into core fuel goods may be conveyed to controller software. Further, management software may receive information related to the core material inserted into cassettes and ready for distribution in inventory. In this manner, management software is able to retain information related to sets of fuel cassettes in inventory and ready for use by consumers.

The Hfuel™ cassettes in inventory may be obtained by consumers through various channels. Particularly, consumers may order small parcel delivery of fuel cassettes. Additionally, consumers may order or obtain fuel cassettes via conventional filling stations. In certain embodiments, the present invention enables consumers to configure a fuel cassette and/or a Decom™ unit to automatically electronically convey ordering information to the management software or a local server, which may process fuel orders. In this manner, the consumer does not need to explicitly order new Hfuel™ cassettes when existing inventories have been exhausted. Upon consumption of available fuel cassette capacity, and if so configured for automatic ordering, the Hfuel™ cassette and/or Decom™ unit can automatically convey ordering information to management software via a memory/telemetry circuit and/or microprocessing unit. Additionally, consumers may explicitly order fuel cassettes via conventional 800 telephone numbers, Internet accessible websites, or other conventional direct order techniques. Additionally, management software may receive information from Decom™ units deployed in various locations in a distribution network. For example, small business or large business Decom™ units may convey fuel usage and requirements information to management software. Also, reseller and consumer Decom™ units may also convey similar information to management software. Finally, management software may also receive and/or convey information between web and Internet data sources or other customer or supplier information sources.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS described herein without departing from the concept, spirit and scope of the invention. More specifically, it will be apparent that certain elements that are related may be substituted for the elements described herein while the same or similar results would be achieved. All such similar substitutes and modifications apparent to those skilled in the art are deemed to be within the spirit, scope and concept of the invention as defined by the appended claims.

What is claimed is:

1. A composition comprising $NaAlH_4$ and $\{\eta^5\text{-}C_5H_5\}_2TiH_2$.

2. The composition of claim 1, wherein the molar ratios of NaH:Al:Ti in the composition are respectively 0.7 to 1.0 to 0.1.

3. The composition of claim 1, wherein the molar ratio of NaH in the composition is between 0.1 and 0.88.

4. The composition of claim 1, wherein the molar ratio of Ti in the composition is between 0.04 and 0.3.

5. The composition of claim 1, wherein the molar ratio of Ti in the composition is equal to (1.0 minus the molar ratio of NaH in the composition) divided by three.

6. The composition of claim 1, wherein the composition has been heated to a temperature of 182° C. or higher.

7. A hydrogen storage system comprising:
   a) a cassette; and
   b) a composition comprising $NaAlH_4$ and $\{\eta^5\text{-}C_5H_5\}_2TiH_2$.

8. The system of claim 7, wherein the cassette contains an opening, the opening sealed with one or more valves.

9. The system of claim 8, wherein the cassette comprises a single two-way valve.

10. The system of claim 8, wherein the cassette comprises two one-way valves.

11. The system of claim 8, wherein the cassette comprises a bidirectional one-way valve.

12. The system of claim 8, wherein a valve opens when hydrogen gas is generated from the composition.

13. The system of claim 8, wherein a valve opens when external hydrogen at a pressure of two or more atmospheres is applied.

14. The system of claim 8, wherein the opening and closing of the one or more valves is electrically controlled.

15. The system of claim 7, further comprising a heater to heat the composition.

16. The system of claim 15, wherein the heater is capable of heating the composition to 100° C.

17. The system of claim 7, further comprising a smart chip.

18. The system of claim 17, wherein the smart chip reports the conditions inside the cassette to an external information processing and control system.

19. The system of claim 18, wherein the conditions are selected from the group consisting of temperature, pressure and the amount of hydrogen charge remaining in the cassette.

20. The system of claim 19, wherein the cassette is installed in a vehicle and the conditions are reported to the operator of the vehicle.

21. The system of claim 7, wherein the system is attached to one or more units selected from the group consisting of a fuel cell, a vehicle, a catalytic heater, a hydrogen combustion device, an emergency power generator, a light, a computer and a portable electronic device.

22. The system of claim 7, further comprising an information processing and control system.

23. A method of preparing a doped sodium alanate composition comprising:
   a) mixing NaH, Al and $\{\eta^5\text{-}C_5H_5\}_2TiH_2$; and
   b) heating the mixture to a temperature above 182° C.

24. The method of claim 23, wherein said mixing occurs in the absence of ball milling.

25. The method of claim 23, wherein the molar ratios of NaH:Al:Ti in the composition are respectively 0.7 to 1.0 to 0.1.

26. The method of claim 23, wherein said heating occurs at a temperature of between 200 and 250° C.

27. The process of claim 23, further comprising performing the process under a noble gas atmosphere.

28. The process of claim 27, wherein the noble gas is argon.

* * * * *